(12) United States Patent
Okano et al.

(10) Patent No.: US 7,919,122 B2
(45) Date of Patent: Apr. 5, 2011

(54) COMPOSITION FOR PRODUCTION OF A STERILIZER AND A PROCESS FOR PRODUCING ORGANIC PERACID

(75) Inventors: Tetsuya Okano, Wakayama (JP); Noboru Matsuo, Wakayama (JP); Chihiro Iwaki, Wakayama (JP); Shigeru Tamura, Wakayama (JP)

(73) Assignee: Kao Corporation, Tokyo (JP)

( * ) Notice: Subject to any disclaimer, the term of this patent is extended or adjusted under 35 U.S.C. 154(b) by 484 days.

(21) Appl. No.: 10/551,654

(22) PCT Filed: Apr. 1, 2004

(86) PCT No.: PCT/JP2004/004809
§ 371 (c)(1),
(2), (4) Date: Jul. 10, 2006

(87) PCT Pub. No.: WO2004/089089
PCT Pub. Date: Oct. 21, 2004

(65) Prior Publication Data
US 2007/0274857 A1    Nov. 29, 2007

(30) Foreign Application Priority Data

Apr. 2, 2003 (JP) ................. 2003-099043
Apr. 2, 2003 (JP) ................. 2003-099044

(51) Int. Cl.
*A61K 33/40* (2006.01)
*C23F 11/10* (2006.01)
*A61L 2/00* (2006.01)
*A61L 9/00* (2006.01)

(52) U.S. Cl. .............. 424/616; 422/17; 422/28; 422/29

(58) Field of Classification Search ................. 424/616; 422/17, 28, 29
See application file for complete search history.

(56) References Cited

U.S. PATENT DOCUMENTS

| | | | |
|---|---|---|---|
| 4,517,159 A * | 5/1985 | Karlson | 422/20 |
| 4,541,944 A | 9/1985 | Sanderson | |
| 5,200,189 A | 4/1993 | Oakes et al. | |
| 5,314,687 A | 5/1994 | Oakes et al. | |
| 5,688,757 A | 11/1997 | Damhus et al. | |
| 5,718,910 A | 2/1998 | Oakes et al. | |
| 5,827,447 A * | 10/1998 | Tamura et al. | 252/186.38 |
| 5,869,440 A * | 2/1999 | Kobayashi et al. | 510/372 |
| 6,221,341 B1 | 4/2001 | Montgomery | |
| 6,399,564 B1 * | 6/2002 | Speed et al. | 510/446 |

FOREIGN PATENT DOCUMENTS

| | | |
|---|---|---|
| EP | 0012578 A1 | 6/1980 |
| EP | 0325184 A1 | 7/1989 |
| EP | 0563460 A1 | 10/1993 |
| JP | 52-25011 A | 2/1977 |
| JP | 52-25034 A | 2/1977 |
| JP | 52-30795 A | 3/1977 |
| JP | 59-205357 A | 11/1984 |
| JP | 62-1792 A | 1/1987 |
| JP | 5-25497 A | 2/1993 |
| JP | 6-305920 A | 11/1994 |
| JP | 8-500843 A | 1/1996 |
| JP | 8-311495 A | 11/1996 |
| WO | WO-93/1716 A1 | 2/1993 |
| WO | WO-93/01716 A1 | 2/1993 |
| WO | WO-94/15465 A1 | 7/1994 |
| WO | WO-94/24869 A1 | 11/1994 |
| WO | WO-01/70030 A1 | 9/2001 |

OTHER PUBLICATIONS

English language abstract of JP 62155203 A (Jul. 10, 1987).
English language abstract of JP 62001796 A (Jan. 7, 1987).

* cited by examiner

*Primary Examiner* — Johann R Richter
*Assistant Examiner* — Abigail Fisher
(74) *Attorney, Agent, or Firm* — Birch, Stewart, Kolasch & Birch, LLP

(57) ABSTRACT

The invention provides a composition for production of a sterilizer having a water content of 1 to 25% by weight and comprising (A) an ester of a polyhydric alcohol and an organic acid having a hydrocarbon group which may have a hydroxyl group and (B1) hydrogen peroxide. From the composition, a sterilizer is obtained as an aqueous solution containing an organic peracid.

13 Claims, No Drawings

COMPOSITION FOR PRODUCTION OF A STERILIZER AND A PROCESS FOR PRODUCING ORGANIC PERACID

FIELD OF THE INVENTION

The present invention relates to a composition for production of a sterilizer, a sterilizer composition and a sterilizing method. Further, the present invention relates to a process for producing an organic peracid used in a sterilizer, a bleaching agent etc. and a process for producing a sterilizer composition.

BACKGROUND OF THE INVENTION

At present, various chemicals exhibiting actions such as bleaching, sterilization and disinfection are known, and particularly hypochlorites such as sodium hypochlorite are used as chlorine type sterilizers, and hydrogen peroxide and sodium percarbonate and sodium perborate generating hydrogen peroxide in water are mainly used as oxygen type sterilizers. However, these sterilizers have various problems; for example, hypochlorites have problems such as corrosion of metal etc. and generation of chlorine gas by misuse, and hydrogen peroxide has problems such as use at high concentration and necessity for long-time contact in order to achieve a sterilizing effect at high degree. When hydrogen peroxide is used, measures to increase a sterilizing effect by using it in combination with an activator to generate an organic peracid at use have been taken to solve these problems. As such a sterilizer composition, JP-A 6-305920 discloses a sterilizer composition containing an inorganic peroxide, an organic acid incomplete ester with a polyhydric alcohol, and an alkaline earth metal salt. For a method of applying an organic peracid as a sterilizer, mention is made of JP-A (W) 8-500843 and JP-A 8-311495. JP-A 5-25497 proposes a method of improving a bleaching effect by adjusting pH in a system of generating an organic peracid. WO-A 01/70030 discloses that a composition containing hydrogen peroxide, a carboxylic acid, and a percarboxylic acid in a specific ratio to the hydrogen peroxide exhibits an antibacterial action on spores and spore-forming microorganisms.

An organic peracid, for example, peracetic acid is produced continuously by reacting hydrogen peroxide with acetic acid under acidic conditions to give an equilibrated mixture containing peracetic acid, acetic acid, hydrogen peroxide and water. Alternatively, peracetic acid can be produced by partial oxidation of acetaldehyde in a gaseous phase or by oxidizing acetaldehyde in the presence of a catalyst to form an intermediate acetaldehyde monoperacetate and then decomposing it in a solvent. JP-A 52-25034 and JP-A 52-25011 disclose a concentrate suitable for sterilization, which contains peracetic acid or acetic acid, hydrogen peroxide, water, etc.

SUMMARY OF THE INVENTION

The present invention relates to a composition for production of a sterilizer, having a water content of 1 to 25% by weight and containing (A) an ester of a polyhydric alcohol and an organic acid having a hydrocarbon group which may have a hydroxyl group and (B1) hydrogen peroxide (referred to hereinafter as the first composition for production of a sterilizer).

The present invention also relates to a composition for production of a sterilizer, which contains (A) an ester of a polyhydric alcohol and an organic acid having a hydrocarbon group which may have a hydroxyl group and (B1) hydrogen peroxide or (B2) an inorganic peroxide releasing hydrogen peroxide in water wherein the molar ratio of (A) to (B1) or the molar ratio of (A) to (B1) generated from (B2), that is, (A)/(B1) is 1/10 to 20/1, the composition for production of a sterilizer being used as an aqueous solution prepared by adjustment to pH 8 to 12 and then to pH 1 to less than 7 (referred to hereinafter as the second composition for production of a sterilizer).

Further, the present invention relates to a composition for production of a sterilizer, obtained by compounding (A) an ester of a polyhydric alcohol and an organic acid having a hydrocarbon group which may have a hydroxyl group and (B1) hydrogen peroxide or (B2) an inorganic peroxide releasing hydrogen peroxide in water wherein the molar ratio of (A) to (B1) or the molar ratio of (A) to (B1) generated from (B2), that is, (A)/(B1) is 1/10 to 20/1, the composition for production of a sterilizer being used as an aqueous solution prepared by adjustment to pH 8 to 12 and then to pH 1 to less than 7 (referred to hereinafter as the third composition for production of a sterilizer).

Further, the present invention relates to a sterilizer composition having a pH value of 1 to less than 7 at 25° C. and containing water and an organic peracid obtained by reacting (A) an ester of a polyhydric alcohol and an organic acid having a hydrocarbon group which may have a hydroxyl group with (B1) hydrogen peroxide in an (A)/(B1) molar ratio of 1/10 to 20/1 in water at pH 8 to 12 (referred to hereinafter as the first sterilizer composition).

The present invention also relates to a method of sterilizing a material to be sterilized, which includes contacting, with a material to be sterilized, an aqueous solution containing an organic peracid obtained by reacting (A) an ester of a polyhydric alcohol and an organic acid having a hydrocarbon group which may have a hydroxyl group with (B1) hydrogen peroxide in an (A)/(B1) molar ratio of 1/10 to 20/1 in water at pH 8 to 12, and then adjusting the reaction system to pH 1 to less than 7.

Furthermore, the present invention relates to a process for producing an organic peracid, which includes a step of reacting (A) an ester of a polyhydric alcohol and an organic acid having a hydrocarbon group which may have a hydroxyl group with (B1) hydrogen peroxide in an (A)/(B1) molar ratio of 1/10 to 20/1 in water at pH 8 to 12, and then adjusting the reaction system to pH 1 to less than 7.

The present invention provides a process for producing an organic peracid-containing sterilizer composition, which includes a step of reacting (A) an ester of a polyhydric alcohol and an organic acid having a hydrocarbon group which may have a hydroxyl group with (B1) hydrogen peroxide in an (A)/(B1) molar ratio of 1/10 to 20/1 in water at pH 8 to 12, and then adjusting the reaction system to pH 1 to less than 7.

The present invention relates to use of the composition for production of a sterilizer described above for production of a sterilizer, and use of the sterilizer composition described above as a sterilizer.

DETAILED DESCRIPTION OF THE INVENTION

JP-A 6-305920 supra does not describe use at a pH value less than pH 7, and there is room for further improvement of the sterilizing effect on spores and fungal spores having higher drug resistance. Each of JP-A (W) 8-500843 and JP-A 8-311495 supra is based on combined use of peracetic acid, acetic acid and hydrogen peroxide at high concentrations as a sterilizer composition, which accompanies an irritative smell to make handling difficult. In JP-A 5-25497 supra, improvements in sterilizing power against spores and fungal spores having higher drug resistance cannot be expected. The composition in WO-A 01/70030 supra, similar to JP-A (W) 8-500843 and JP-A 8-311495, accompanies an irritative smell as well to make its handling problematic.

It can be hardly said that the amount of remaining hydrogen peroxide in conventional sterilizers using an organic peracid has been sufficiently regulated in their production methods by taking a suitable balance among starting materials into consideration. As described above, when acetic acid is reacted with hydrogen peroxide, the reaction product is obtained as an equilibrated mixture containing hydrogen peroxide, thus having a relatively higher concentration of hydrogen peroxide. Accordingly, an aqueous solution of an organic peracid produced by a conventional method tends to contain a relatively higher concentration of an unreacted hydrogen peroxide component. Such an increase in the concentration of hydrogen peroxide per unit amount leads to a decrease in the concentration of an organic peracid, and is thus disadvantageous in sterilization at a higher level. Nowadays, a reduction in burden on the environment is an urgent task, but the sterilizers containing hydrogen peroxide in excess require treatments such as neutralization, decomposition etc. prior to discharge, and such treatment costs become a significant burden.

The present invention provides a composition for production of a sterilizer which can give a sterilizer composition generating a high concentration of an organic peracid efficiently and stably at use to show high sterilizing power, as well as a sterilizer composition showing high sterilizing power.

Hereinafter, (A) an ester of a polyhydric alcohol and an organic acid having a hydrocarbon group which may have a hydroxyl group is referred as the component (A); (B1) hydrogen peroxide is referred to as the component (B1); (B2) an inorganic peroxide releasing hydrogen peroxide in water is referred to as the component (B2); and the components (B1) and (B2) are collectively referred to as the component (B).

The number of moles of hydrogen peroxide generated from the component (B2) in the component (B) is a value obtained by multiplying the amount (g) of the component (B2) incorporated into the composition, by the concentration (wt %) of hydrogen peroxide in the component (B2) determined by titration with permanganic acid, and dividing the product by 34 that is the molecular weight of hydrogen peroxide.

The present invention provides a composition for production of a sterilizer showing high sterilizing power not only against general microorganisms but also against highly drug-resistant spores and fungal spores.

A sterilizer composition obtained from the composition for production of a sterilizer according to the present invention, or the sterilizer composition according to the present invention, has a high sterilizer effect and is excellent in durability thereof. According to the present invention, there is provided a sterilizing method showing a sterilizing effect in a wide variety of fields ranging from industrial sterilization in food factories etc. to sterilization in homes.

<Component (A)>

As the component (A), the ester of a polyhydric alcohol and an organic acid having a hydrocarbon group which may have a hydroxyl group reacts with hydrogen peroxide to generate an organic peracid.

The polyhydric alcohol for constituting the component (A) is preferably a C2 to C12 alcohol, and examples thereof include glycerin derivatives such as glycerin, diglycerin and triglycerin, and sugars such as glucose, sucrose, fructose, sorbitol, pentaerythritol, alkyl polyglycoside and alkyl furanoside.

The organic acid for constituting the component (A) includes aliphatic monocarboxylic acids such as acetic acid, propionic acid, butyric acid, valeric acid, caproic acid and octanoic acid, aliphatic dicarboxylic acids such as oxalic acid, malonic acid, succinic acid, maleic acid and fumaric acid, and hydroxycarboxylic acids such as citric acid, tartaric acid and malic acid, and is preferably a C1 to C8 saturated or unsaturated aliphatic mono- or dicarboxylic acid, more preferably a C1 to C8 saturated or unsaturated aliphatic monocarboxylic acid, still more preferably a C1 to C8 fatty acid, furthermore preferably a C2 to C8 fatty acid. The degree of esterification of the component (A) is not limited.

Specifically, the component (A) is preferably an ester of glycerin and a C1 to C8 aliphatic monocarboxylic acid, more preferably triacetin.

<Component (B)>

The component (B) is (B1) hydrogen peroxide or (B2) an inorganic peroxide releasing hydrogen peroxide in water, and when the composition is a liquid form, hydrogen peroxide is preferable, and when the composition is in a solid form such as particles or powder, percarbonate or perborate is preferable, and sodium percarbonate or sodium perborate is particularly preferable.

<First Composition for Production of a Sterilizer>

The first composition for production of a sterilizer according to the present invention contains the components (A) and (B1), and from the viewpoint of maintaining the stability of the composition by suppressing the reaction of the component (A) with the component (B1) during storage, the water content of the composition is preferably 1 to 25% by weight, more preferably 5 to 20% by weight, still more preferably 5 to 15% by weight.

The first composition for production of a sterilizer according to the present invention is a liquid composition of one-pack type containing the components for giving an organic peracid, and is thus preferable for example in production of the first sterilizer composition of the invention described later or an aqueous solution for sterilization used in the sterilizing method of the invention. In the first composition for production of a sterilizer, the content of the component (A) is preferably 20 to 90% by weight, more preferably 30 to 90% by weight, still more preferably 40 to 80% by weight, and the content of the component (B1) is preferably 1 to 30% by weight, more preferably 5 to 25% by weight, still more preferably 10 to 25% by weight. The molar ratio of the component (A) to the component (B1), that is, (A)/(B1) is preferably 1/10 to 20/1, more preferably 1/10 to 10/1, still more preferably 1/5 to 10/1. The molar ratio of the component (B1) to one ester group of the component (A) is preferably 2 or less, more preferably 0.3 to 2, from the viewpoint of efficient formation of an organic peracid and reduction of unreacted hydrogen peroxide.

If necessary, the first composition for production of a sterilizer can contain a chelating agent, a pH adjusting agent, a solvent etc. The chelating agent is useful for suppression of the catalytic decomposition caused by contamination with a very small amount of metallic ions such as Fe and Cr. The pH value (20° C.) of a stock solution of the first composition for production of a sterilizer is preferably 0.5 to 6, more preferably 1 to 5, still more preferably 1 to 4, from the viewpoint of storage stability. The chelating agent is preferably an agent also having an action to serve as a pH adjusting agent, and preferable examples include phosphoric acid, polymerized phosphoric acid, organic phosphonic acid, aminocarboxylic acid, hydroxycarboxylic acid, and salts thereof. In particular, organic phosphonic acid or its salt is preferable. The solvent is preferably a polyhydric alcohol solvent, particularly preferably a glycol solvent such as propylene glycol.

<Second Composition for Production of a Sterilizer>

The second composition for production of a sterilizer according to the present invention contains the components (A) and (B), wherein the ratio of the two is preferably in such a range that the component (B1) reacts efficiently with the component (A), and in consideration of the efficiency of formation of an organic peracid, the sterilizing effect, the stability of the preparation, etc., the molar ratio of the component (A) to the component (B1), that is, (A)/(B1) is preferably 1/10 to 20/1, more preferably 1/10 to 10/1, still more preferably 1/5 to 10/1. The molar ratio of the component (B1) to one ester group of the component (A) is preferably 2 or less, more preferably 0.3 to 2, from the viewpoint of efficient formation of an organic peracid and reduction of unreacted hydrogen peroxide. When the component (B2) is used, it is compounded preferably in such an amount as to generate the component (B1) in the range described above.

Preferably, the second composition for production of a sterilizer according to the present invention not only satisfies this molar ratio, but also contains the component (A) in an amount of 0.1 to 90% by weight, preferably 0.5 to 70% by weight, more preferably 1 to 50% by weight and the component (B) as the component (B1) in an amount of 0.1 to 50% by weight, preferably 0.1 to 30% by weight, more preferably 0.1 to 20% by weight.

The second composition for production of a sterilizer according to the present invention, when used, is adjusted to pH 8 to 12, preferably pH 9 to 11 (first step) and then to pH 1 to less than 7, preferably pH 1 to 6, more preferably pH 1 to 5 (second step), to prepare an aqueous solution of a sterilizer composition. Preferably, an alkaline pH adjusting agent is used in the first step, and an acidic pH adjusting agent in the second step. This pH may be a pH value at use, but preferably satisfies the above pH at 25° C. The first composition for production of a sterilizer according to the present invention can also be similarly used.

The alkaline pH adjusting agent includes alkali metal hydroxides or alkaline earth metal hydroxides such as sodium hydroxide, potassium hydroxide, calcium hydroxide, barium hydroxide etc., alkali metal silicates such as sodium silicate, potassium silicate etc., alkali metal phosphates showing alkalinity, such as trisodium phosphate etc., and alkali metal carbonates such as sodium carbonate, potassium carbonate etc., among which alkali metal hydroxides such as sodium hydroxide and potassium hydroxide, alkali metal phosphates such as trisodium phosphate and tripotassium phosphate, and alkali metal carbonates such as sodium carbonate and potassium carbonate are preferable from the viewpoint of alkalinity and water solubility. The acidic pH adjusting agent includes inorganic acids such as hydrochloric acid, sulfuric acid, phosphoric acid etc., and organic acids such as formic acid, acetic acid, citric acid, succinic acid, gluconic acid etc., among which liquid inorganic acids such as sulfuric acid and phosphoric acid and highly water-soluble organic acids such as citric acid and acetic acid are preferable from the viewpoint of acidity and water solubility. These can be used singly or a mixture of two or more thereof. These pH adjusting agents may be present in the second composition for production of a sterilizer according to the present invention. These pH adjusting agents can also be present in the above-described first composition for production of a sterilizer according to the present invention.

The second composition for production of a sterilizer according to the present invention can contain a surfactant, inorganic or organic salts, a chelating agent, a perfume, a pigment, a dye etc. in addition to the components (A) and (B). These components can also be present in the above-described first composition for production of a sterilizer according to the present invention.

The surfactant includes nonionic surfactants, anionic surfactants, cationic surfactants and amphoteric surfactants. The nonionic surfactants include monohydric alcohol derivative-based nonionic surfactants such as polyoxyethylene (referred to hereinafter as POE) alkyl ether, POE alkyl phenyl ether, polyoxypropylene/POE (block or random) alkyl ether, POE aryl phenyl ether, POE styrene phenyl ether, POE tribenzyl phenyl ether, etc., and polyhydric alcohol derivative-based nonionic surfactants such as (poly)glycerin fatty ester, sucrose fatty ester, sorbitan fatty ester, alkyl polyglycoside, etc. The anionic surfactants include lignin sulfonate, alkyl benzene sulfonate, alkyl sulfonate, POE alkyl sulfonate, POE alkyl phenyl ether sulfonate, POE alkyl phenyl ether phosphate, POE aryl phenyl ether sulfonate, POE aryl phenyl ether phosphate, naphthalene sulfonate, naphthalene sulfonic acid/formalin condensates, POE tribenzyl phenyl ether sulfonate, POE tribenzyl phenyl ether phosphate, etc. The cationic surfactants include mono-long chain alkyl (C8 to C18) trimethyl ammonium chloride, di-long chain alkyl (C8 to C18) dimethyl ammonium chloride, benzalkonium chloride, benzethonium chloride, etc. The amphoteric surfactants include alkyl aminotrimethyl glycine, alkyl dimethyl amine oxide, alkyl diaminoethyl glycine hydrochloride, etc. These can be used singly or as a mixture of two or more thereof. The surfactant is preferably a nonionic surfactant, more preferably a polyhydric alcohol-based nonionic surfactant. The surfactant is contained in an amount of preferably 0 to 20% by weight, more preferably 0 to 10% by weight, in the second composition for production of a sterilizer according to the present invention.

The salts not only serve as a pH adjusting agent, but are also used mainly for the purpose of stabilization of the sterilizer, and specific examples include organic salts such as metal salts of carboxylic acids such as succinic acid, malonic acid, citric acid, gluconic acid, glutaric acid etc., metallic salts of phosphoric acid compounds such as tripolyphosphoric acid, hexamethaphosphoric acid, phosphoric acid etc., and inorganic salts such as sulfates such as sodium sulfate, potassium sulfate etc. These can be used singly or as a mixture of two or more thereof.

The chelating agent includes ethylenediaminetetraacetic acid, nitrotriacetic acid, tripolyphosphoric acid, polyhydroxyacrylic acid, organic phosphonic acid or salts thereof.

The second composition for production of a sterilizer according to the present invention can have various forms, and in the case of a liquid form, the composition is preferably highly fluidic and may be in the form of fluidic slurry, gel, paste or the like besides the aqueous solution. When the composition is in a solid form, it may be in the form of particles, powder, granules, pellets etc.

The second composition for production of a sterilizer according to the present invention may contain all compounding ingredients packaged together therein, but from the viewpoint of stability, is preferably a multi-pack type wherein the components (A) and (B) are separately packaged. The composition can be for example a composition of 3-pack type for production of a sterilizer, containing a package (1) of a composition containing the component (A), a package (2) of a composition containing the component (B) and a package (3) of a composition containing a pH adjusting agent (acidic pH adjusting agent such as citric acid) for final adjustment to pH 1 to less than 7. In this case, a mixture of the packages (1) and (2) is regulated preferably in the range of pH 8 to 12 by incorporation of an alkali into the package (2). Particularly when the composition is in a powdery form, the components (A) and (B) can be coexistent in one package, and the composition can be for example a composition of 2-pack type for production of a sterilizer, containing a package (I) of a composition containing the components (A) and (B) and an alkali for adjustment to pH 8 to 12 and a package (II) of a composition containing a pH adjusting agent (acidic pH adjusting agent such as citric acid) for final adjustment to pH 1 to less than 7.

The pH of the second composition for production of a sterilizer according to the present invention, when used, is regulated in the first and second steps, whereby an aqueous solution of a sterilizer composition containing an organic peracid is prepared. The concentration of an organic peracid in the aqueous solution is preferably 10 to 20,000 ppm (ratio by weight; this hereinafter applies), more preferably 10 to 10,000 ppm. In respect of the sterilizing effect, the content of hydrogen peroxide in the aqueous solution is preferably 0.5 wt % or less, more preferably 0.3 wt % or less, still more preferably 0.2 wt % or less. These findings also apply to the first composition for production of a sterilizer according to the present invention.

<Third Composition for Production of a Sterilizer>

The third composition for production of a sterilizer according to the present invention is obtained by compounding the above-mentioned components (A) and (B) in the present invention wherein similarly to the second composition for production of a sterilizer, the molar ratio of the component (A) to the component (B1) derived from the component (B), that is, (A)/(B1) is 1/10 to 20/1, the composition for production of a sterilizer being used as an aqueous solution prepared by adjustment to pH 8 to 12 and then to pH 1 to less than 7. Specific compounds of the components (A) and (B) and the preferable (A)/(B1) molar ratio are the same as in the second composition for production of a sterilizer. The third composition for production of a sterilizer can also contain the above-mentioned surfactant, inorganic or organic salts, chelating agent, perfume, pigment and dye, and the mode of packaging can also be the same as described above.

<First Sterilizer Composition>

The first sterilizer composition of the present invention contains water and an organic peracid obtained by reacting the component (A) with the component (B1) in an (A)/(B1) molar ratio of 1/10 to 20/1 in water at pH 8 to 12, the sterilizer composition having a pH value of 1 to less than 7 at, 25° C. As described above, the first sterilizer composition of the present invention is prepared by reacting the components (A) and (B1) in a specific molar ratio in water at pH 8 to 12, and subsequent adjustment to pH 1 to less than 7, preferably pH 1 to 6, more preferably pH 1 to 5. Specific compounds of the components (A) and (B) and the preferable (A)/(B1) molar ratio are the same as in the second composition for production of a sterilizer according to the present invention. The first sterilizer composition can also contain the surfactant, inorganic or organic salts, chelating agent, perfume, pigment and dye described above. The amount of water in the composition is preferably 50 wt % to less than 100 wt %, more preferably 60 wt % to less than 100 wt %, still more preferably 70 wt % to less than 100 wt %. Similar to the aqueous solution obtained from the composition for production of a sterilizer according to the present invention, the first sterilizer composition of the present invention is an aqueous solution containing an organic peracid, and the concentration of an organic peracid in the aqueous solution is preferably 10 to 20,000 ppm, more preferably 10 to 10,000 ppm. In respect of the sterilizing effect, the content of hydrogen peroxide in the first sterilizer composition of the present invention is preferably 0.5 wt % or less, more preferably 0.3 wt % or less, still more preferably 0.2 wt % or less. This hydrogen peroxide content is achieved preferably just after preparation of the composition, more preferably at use.

<Sterilizing Method>

The sterilizing method of the present invention includes contacting, with a material to be sterilized, an organic peracid-containing aqueous solution (hereinafter, referred to as an aqueous solution for sterilization) obtained by reacting the component (A) with the component (B1) in an (A)/(B1) molar ratio of 1/10 to 20/1 in water at pH 8 to 12, and then adjusting the reaction system to pH 1 to less than 7, preferably pH 1 to 6, more preferably pH 1 to 5, wherein the sterilizer composition of the present invention, or the composition for production of a sterilizer according to the present invention, is preferably used.

The sterilizing method of the present invention can include:

(I) a step of reacting the component (A) with the component (B1) in an (A)/(B1) molar ratio of 1/10 to 20/1 in water at pH 8 to 12 to give an aqueous solution containing an organic peracid, (II) a subsequent step of adjusting the aqueous solution to pH 1 to less than 7, preferably pH 1 to 6, more preferably pH 1 to 5 to give an aqueous solution for sterilization, and (III) a step of contacting the aqueous solution for sterilization with a material to be sterilized.

The step (I) above can be carried out by adding predetermined amounts of the components (A) and (B1) and a pH adjusting agent (alkali) giving pH 8 to 12, for example to water at 5 to 50° C. and reacting the component (A) with the component (B1). The step (II) above can be carried out by adding a pH regulating agent (acid) giving pH 1 to less than 7 to the mixture system.

The method of contacting the aqueous solution for sterilization with a material to be sterilized involves sprinkling, dipping, charging or applying the aqueous solution. When the aqueous solution is sprinkled, spraying is preferable. Alternatively, a suitable carrier may be impregnated with the aqueous solution and used to wipe an object. Although the contact time is not limited, a sufficient effect can be attained in a short time of 30 seconds or less, particularly 10 seconds or less, depending on a material to be sterilized. The temperature of the aqueous solution to be contacted is not limited either, but is preferably 10 to 90° C., more preferably 15 to 80° C.

The sterilizer composition of the present invention, or a sterilizer (aqueous solution for sterilization) obtained from the composition for production of a sterilizer, or the sterilizing method has a high sterilizing effect, and can thus be applied to a wide variety of materials containing various microorganisms as a subject of sterilization. Examples include microorganisms causing food born diseases and hospital infections, such as *Escherichia coli, Salmonella, Staphylococcus aureus, Pseudomonas aeruginosa* etc., fungi such as *Aspergillus niger, Candida* etc., and microbial spores of *Bacillus subtilis* and fungal spores of *Aspergillus niger* having high resistance to sterilizers. Among these, the microbial spores are durable sleeper cells produced under an environment unsuitable for growth, and have multi-layered outer shells outside of the microbial body. Such microbial spores are extremely durable to drug and heat and hardly completely extinguishable by general sterilization. However, the sterilizer composition or the sterilizing method according to the present invention can give a sufficient sterilizing effect on such microbial spores.

As described above, the sterilizer composition, the sterilizer (aqueous solution for sterilization) obtained from the composition for production of a sterilizer, or the sterilizing method according to the present invention has a wide bactericidal spectrum, exhibits a strong effect not only on microorganisms but also on fungi and spores, and is thus useful for sterilization in a wide variety of fields. It can be used for example on walls, floors, windows etc. in hospitals, nursing institutions, food processing factories, cleaning facilities, kitchens, as well as instruments, equipments, and product (e.g. drink) containers etc. used therein.

<Sterilizer Kit>

A sterilizer kit preferable for obtaining the sterilizer composition of the present invention is constituted by incorporation of the composition for production of a sterilizer according to the present invention, a reaction initiator [referred to hereinafter as component (C)] initiating the components (A) and (B1) brought about by the composition, and a pH adjusting agent [referred to hereinafter as component (D)]. The sterilizer kit can also constituted by incorporation of the components (A), (B), (C) and (D).

The sterilizer kit for obtaining the sterilizer composition of the present invention may be a kit of one-pack type containing all compounding ingredients together packaged therein in consideration of simplicity at the time of production of an organic peracid, or a kit of multi-pack type containing the components (A), (B), (C) and (D) packaged in preparations different from one another in consideration of stability during storage. In consideration of both simplicity at the time of production of an organic peracid and the storage stability of the composition for production, the preparation form of the sterilizer kit is preferably a two-pack type or a multi-pack type such as a three-pack type, containing packages each having a composition containing two or more of the components (A) to (D) packaged therein.

The components (A) and (B1) react with each other under alkaline conditions in water (preferably at a water temperature of 5 to 50° C.) to form an organic peracid, and thus a component giving such pH can be used as the component (C). Specific examples include the alkaline pH adjusting agents illustrated above, that is, alkali metal hydroxides or alkaline earth metal hydroxides such as sodium hydroxide, potassium hydroxide, calcium hydroxide, barium hydroxide etc., alkali metal silicates such as sodium silicate, potassium silicate etc., alkali metal phosphates showing alkalinity, such as trisodium phosphate etc., and alkali metal carbonates such as sodium carbonate, potassium carbonate etc., among which alkali metal hydroxides such as sodium hydroxide and potassium hydroxide, alkali metal phosphates such as trisodium phosphate and tripotassium phosphate, and alkali metal carbonates such as sodium carbonate and potassium carbonate are preferable from the viewpoint of alkalinity and water solubility.

On one hand, the sterilizer containing an organic peracid is preferably acidic in respect of the sterilizing effect, and thus a component capable of adjusting the pH rendered alkaline by the component (C) to the acidic range is used as the component (D). Specific examples include the acidic pH adjusting agents illustrated above, that is, inorganic acids such as hydrochloric acid, sulfuric acid, phosphoric acid etc., and organic acids such as formic acid, acetic acid, citric acid, succinic acid, gluconic acid etc., among which liquid inorganic acids such as sulfuric acid and phosphoric acid and highly water-soluble organic acids such as citric acid and acetic acid are preferable from the viewpoint of acidity and water solubility.

The specific preparation form of the sterilizer kit includes:
(I) a 3-pack or more preparation form containing a package (X1) of a composition for production of a sterilizer containing the components (A) and (B), a package (X2) of a composition containing the component (C), and a package (X3) of a composition containing the component (D),
(II) a 3-pack or more preparation form containing a package (Y1) of a composition containing the component (A), a package (Y2) of a composition containing the components (B) and (C), and a package (X3) of a composition containing the component (D), and
(III) a 2-pack or more preparation form containing a package (Z1) of a composition containing the components (A), (B) and (C) and a package (Z2) of a composition containing the component (D).

The composition for production of a sterilizer, in the case of the preparation form (I), is not limited and may be in the form of powder, solid, liquid or the like, but is preferably in the form of liquid from the viewpoint of simplicity. When the composition is in the form of liquid, the water content of the liquid composition is preferably 1 to 25% by weight, more preferably 5 to 20% by weight, still more preferably 5 to 15% by weight, from the viewpoint of maintaining the stability of the composition by suppressing the reaction of the component (A) with the component (B) during storage. If necessary, a chelating agent and a solvent can be added to the liquid composition. The chelating agent is useful for suppressing the catalytic decomposition caused by contamination with a very small amount of metallic ions such as Fe and Cr. The pH value (20° C.) of a stock solution of the liquid composition is preferably 0.5 to 6, more preferably 1 to 5, still more preferably 1 to 4, in order to participate in storage stability. As described above, the chelating agent is preferably an agent also having an action to serve as a pH adjusting agent, and preferable examples include phosphoric acid, polymerized phosphoric acid, organic phosphonic acid, aminocarboxylic acid, hydroxycarboxylic acid, and salts thereof. In particular, organic phosphonic acid or its salt is preferable. The solvent is preferably a polyhydric alcohol solvent, particularly preferably a glycol solvent such as propylene glycol.

When the composition for production of a sterilizer, in the case of the preparation form (I), is in the form of powder or solid, sodium percarbonate, sodium perborate or the like is preferably used. Similarly, the composition containing the component (B), whether in the preparation form (II) or (III), is preferably in the form of powder or solid containing sodium percarbonate, sodium percarbonate or the like as the component (B), from the viewpoint of storage stability.

The content of the components (A) to (D) in each preparation form can be determined in a suitable range on the basis of usage of the first to third compositions for production of a sterilizer according to the present invention. Components other than the components (A) to (D) may be incorporated into any packages containing the components (A) to (D) or into other packages.

The present invention provides a method wherein an organic peracid exhibiting high stability and sterilizing power and preferable as a sterilizer or the like can be produced without using hydrogen peroxide in excess. Hereinafter, this production method is described in detail.

According to the present invention, an organic peracid highly effective as a sterilizer or the like can be produced efficiently without using an excess of hydrogen peroxide. Accordingly, an aqueous organic peracid solution with a lower content of hydrogen peroxide can be obtained, and can thus reduce the burden of waste fluid on the environment when used for example as a sterilizer.

<Component (A)>

It can be used in the same manner as for the component (A) in the composition described above.

<Component (B)>

The component (B) is hydrogen peroxide (B1), and an inorganic peroxide releasing hydrogen peroxide in water may be dissolved water and used as the component (B). The inorganic peroxide is preferably a percarbonate, especially a perborate, particularly sodium percarbonate or sodium perborate.

<Production Process>

When the component (A) is reacted with the component (B1) in the production process of the present invention, the molar ratio of the two is a specified ratio, and the pH in the reaction system is changed in 2 stages. The production process of the present invention, which is different from a conventional process wherein acetic acid is reacted with hydrogen peroxide, is advantageous in that since the reaction between the component (A) and the component (B1) is an irreversible reaction, an aqueous solution containing an organic peracid at desired concentration is produced without accumulation of hydrogen peroxide in the system. That is, the present invention can provide a process for producing an aqueous solution containing an organic peracid, which includes a step of reacting the component (A) with the component (B1) in the above-specified molar ratio in water at pH 8 to 12, and then adjusting the reaction system to pH 1 to less than 7.

From the viewpoint of stability and efficient formation of an organic peracid, it is preferable that the molar ratio of the component (A) to the component (B1), that is, (A)/(B1) is 1/10 to 20/1, preferably 1/10 to 10/1, more preferably 1/5 to 10/1. The molar ratio of the component (B1) to one ester group of the component (A) is preferably 2 or less, more preferably 0.3 to 2, from the viewpoint of efficient formation of an organic peracid and reduction of unreacted hydrogen peroxide.

The ratio of the components (A) and (B1) to water by weight, that is, [(A)+(B1)]/water is preferably 1/10000 to 1/1, more preferably 1/1000 to 1/2.

Preferably, the composition not only satisfies the above molar ratio or weight ratio, but is also charged with the component (A) in an amount of 0.1 to 90% by weight, more preferably 0.5 to 70% by weight, still more preferably 1 to 50% by weight, and the component (B1) in an amount of 0.1 to 50% by weight, more preferably 0.1 to 30% by weight, still more preferably 0.1 to 20% by weight, in the reaction system.

In the process of the present invention, a liquid composition with a water content of 1 to 25% by weight containing the components (A) and (B1) is preferably used. That is, in the process of the present invention, the components (A) and (B1) are brought about preferably as a liquid composition with a water content of 1 to 25% by weight containing the components (A) and (B1). In the liquid composition, the content of the component (A) is preferably 20 to 90% by weight, more preferably 30 to 90% by weight, still more preferably 40 to 80% by weight, and the content of the component (B1) is preferably 1 to 30% by weight, more preferably 5 to 25% by weight, still more preferably 10 to 25% by weight. The molar ratio of the component (A) to the component (B1), that is, (A)/(B1) is preferably 1/10 to 20/1, more preferably 1/10 to 10/1, still more preferably 1/5 to 10/1. The molar ratio of the component (B1) to one ester group of the component (A) is preferably 2 or less, more preferably 0.3 to 2, from the viewpoint of efficient formation of an organic peracid and reduction of unreacted hydrogen peroxide.

If necessary, the liquid composition can contain a chelating agent, a pH adjusting agent, a solvent etc. The chelating agent is useful for suppressing the catalytic decomposition caused by contamination with a very small amount of metallic ions such as Fe and Cr. The pH value (20° C.) of a stock solution of the liquid composition is preferably 0.5 to 6, more preferably 1 to 5, still more preferably 1 to 4, from the viewpoint of storage stability. The chelating agent is preferably an agent also having an action to serve as a pH adjusting agent, and preferable examples include phosphoric acid, polymerized phosphoric acid, organic phosphonic acid, aminocarboxylic acid, hydroxycarboxylic acid, and salts thereof. In particular, organic phosphonic acid or its salt is preferable. The solvent is preferably a polyhydric alcohol solvent, particularly preferably a glycol solvent such as propylene glycol.

As the component (B), it is possible to employ the component obtained from a granular, powdery or solid composition containing an inorganic peroxide releasing hydrogen peroxide in water, for example, a percarbonate or a perborate, particularly sodium percarbonate or sodium perborate.

In the present invention, the component (A) is mixed with the component (B), and then the reaction system is adjusted to pH 8 to 12, preferably pH 9 to 11 (first step) and then to pH 1 to less than 7, preferably pH 1 to 6, more preferably pH 1 to 5 (second step). Preferably, an alkaline pH adjusting agent is used in the first step, and an acidic pH adjusting agent in the second step. This pH is a pH value at the time of reaction, and preferably the final product after the reaction satisfies the pH value of the second step at 25° C.

The first step is a step of generating an organic peracid, and the time therefor is not limited, wherein the reaction system is kept at pH 8 to 12 until 50% of the theoretical amount of an organic peracid is generated. The reaction time in the first step is preferably 1 to 120 minutes. The reaction temperature in the first step is preferably 5 to 50° C.

The second step is a step of stabilizing the generated organic peracid, and is carried out essentially by adding a pH adjusting agent for adjustment to pH 1 to less than 7 to the reaction system. That is, when the pH reaches a predetermined value, the second step is finished. The reaction temperature in the second step is preferably 5 to 50° C.

According to the process of the present invention, the organic peracid can be obtained in an aqueous solution, and the concentration of remaining hydrogen peroxide in the aqueous solution is preferably 60 wt % or less, more preferably 50 wt % or less and still more preferably 0.1 to 50 wt % of the amount of initially charged hydrogen peroxide, from the viewpoint of preventing accumulation of hydrogen peroxide and stability of the organic peracid.

The alkaline pH adjusting agent can be used in the same manner as in the composition described above. The pH adjusting agent may remain in the organic peracid-containing aqueous solution produced in the present invention.

In the present invention, the reaction system can be charged with a surfactant, inorganic or organic salts, a chelating agent, a perfume, a pigment, a dye etc. in addition to the components (A) and (B). A sterilizer, a bleaching agent etc. can thereby be easily obtained.

The surfactant can be used in the same manner as in the composition described above. The surfactant is contained in an amount of preferably 0 to 20% by weight, more preferably 0 to 10% by weight, in the reaction system in the present invention.

The salts and the chelating agent can also be used in the same manner as in the composition described above.

The organic peracid-containing aqueous solution obtained by the present invention can have various forms, and the aqueous solution in a liquid form is preferably highly fluidic and may be in the form of fluidic slurry, gel, paste or the like besides the aqueous solution.

The organic peracid concentration of the organic peracid-containing aqueous solution obtained by the present invention is preferably 10 to 100,000 ppm (ratio by weight; this hereinafter applies), more preferably 10 to 50,000 ppm.

In the case of a sterilizer, for example, an organic peracid at a necessary concentration can be easily obtained at use by using the compounding ingredients such that the process of the present invention is carried out.

In the case of a sterilizer, the organic peracid-containing aqueous solution obtained by the present invention may be used as it is, but from an economical viewpoint, is preferably diluted suitably with water for use as an aqueous solution at an organic peracid concentration of 10 to 20,000 ppm, particularly 10 to 10,000 ppm.

When the organic peracid obtained by the process of the present invention is used as a sterilizer, the organic peracid-containing aqueous solution (referred to hereinafter as an aqueous solution for sterilization) is contacted with a material to be sterilized.

The method of bringing the aqueous solution for sterilization into contact with a material to be sterilized is the same as in the composition described above.

The aqueous solution for sterilization is a sterilizer composition, and the content of hydrogen peracid in the composition is preferably 0.5 wt % or less, more preferably 0.3 wt % or less, more preferably 0.2 wt % or less.

The organic peracid produced by the present invention, similar to the composition described above, has a high sterilizing effect and can thus be applied to a wide variety of materials containing various microorganisms as a subject of sterilization.

As described above, the organic peracid produced by the present invention, similar to the composition described above, has a wide bactericidal spectrum, exhibits a strong effect not only on microorganisms but also on fungi and spores, and is thus useful in a wide variety of fields.

EXAMPLE 1

The components (A) and (B) in the amounts shown in Tables 1 to 5, 50 g deionized water and a suitable amount of an alkaline pH adjusting agent [sodium carbonate] were mixed for 20 minutes with stirring in a 200 mL beaker. The pH value in this step was controlled in the range of 8 to 12. Thereafter, the mixture was adjusted to the objective pH value by using an acidic pH adjusting agent [citric acid] to give a sterilizer composition. A change in the organic peracid concentration with time in this process was measured. The organic peracid concentration was measured by the following method. The results are shown in Tables 1 to 5.

(1) Method of Measuring the Concentration of an Organic Peracid (1-1) Quantification of Hydrogen Peroxide $w_1$ g (for example, 1 to 50 g) of the sterilizer composition was accurately weighed out in a 200 mL conical beaker, and 10 mL of 20% aqueous sulfuric acid solution and 2 to 3 ice pieces were added thereto to cool the solution, and after 1 to 2 drops of an aqueous saturated manganese sulfate solution were added thereto as a catalyst, the solution was titrated with 0.1 mol/L (½ N) aqueous potassium permanganate solution. The point in time when the solution assumed a pale pink color for 1 to 10 seconds was regarded as end point. The hydrogen peroxide concentration is calculated from the following equation (1-1)

$$\text{Hydrogen peroxide concentration(wt \%)} = (0.85 \times T_1 \times F_1)/w_1 \quad (1\text{-}1)$$

$T_1$: amount (mL) of 0.1 mol/L aqueous potassium permanganate solution required in titration $F_1$: factor of 0.1 mol/L aqueous potassium permanganate solution $w_1$: weight (g) of the sterilizer composition (1-2) Quantification of an Organic Peracid $w_2$ g (for example, 1 to 50 g) of the sterilizer composition was accurately weighed out in a 300 mL Erlenmeyer flask equipped with a cap, and after 10 mL of 20% aqueous sulfuric acid solution, 20 mL purified water and 2 mL aqueous saturated potassium iodide solution were added thereto, the flask was capped and then gently shaken. The solution was left in a cool and dark place for 5 minutes and then titrated with 0.2 mol/L (⅕ N) aqueous sodium thiosulfate solution. When the solution assumed a pale yellow color, the titration was continued by adding a few drops of 2% aqueous starch solution. The point in time when the bluish violet color of the solution disappeared was regarded as end point. The organic peracid concentration is calculated from the following equation (1-2):

$$\text{Organic peracid concentration(wt \%)} = (\text{molecular weight of organic peracid} \times [\{T_2 \times F_2\}/\{100 \times w_2\} - H/34])/\text{number of percarboxyl groups in one molecule} \quad (1\text{-}2)$$

$T_2$: amount (mL) of 0.2 mol/L aqueous sodium thiosulfate solution required in titration $F_2$: factor of 0.2 mol/L aqueous sodium thiosulfate solution H: hydrogen peroxide concentration (wt %) determined by formula (1-1)

$w_2$: weight (g) of the sterilizer composition

TABLE 1

| | | | Products of the invention | | | | |
|---|---|---|---|---|---|---|---|
| | | | 1-1 | 1-2 | 1-3 | 1-4 | 1-5 |
| Compounding component | (A) | Ethylene glycol monoacetate | 2 g (0.0192) | | | | |
| | | Ethylene glycol diacetate | | 2 g (0.0137) | | | |
| | | Diacetin | | | 2 g (0.0114) | | |
| | | Triacetin | | | | 2 g (0.0092) | |
| | | Pentaerythritol tetraacetate | | | | | 2 g (0.0066) |
| | | Pentaacetyl-β-D-glucose | | | | | |
| | | Glycerine fatty acid ester | | | | | |

TABLE 1-continued

|  |  |  |  |  |  |  |  |
|---|---|---|---|---|---|---|---|
|  | (B) | Aqueous hydrogen peroxide (35 wt %) | 2.86 g (0.0294) | 2.86 g (0.0294) | 2.86 g (0.0294) | 2.86 g (0.0294) | 2.86 g (0.0294) |
|  |  | Sodium percarbonate |  |  |  |  |  |
|  |  | Sodium perborate |  |  |  |  |  |
| (A)/(B) molar ratio |  |  | 0.65 | 0.47 | 0.39 | 0.31 | 0.22 |
| pH(25° C.) |  |  | 4.0 | 4.0 | 4.0 | 4.0 | 4.0 |
| Organic peracid concentration (ppm) |  | Just after pH adjustment | 6900 | 17000 | 10000 | 22900 | 4500 |
|  |  | 30 minutes after pH adjustment | 6800 | 17000 | 9600 | 20300 | 4500 |
|  |  | 60 minutes after pH adjustment | 6600 | 16800 | 9100 | 18600 | 4300 |
|  |  | 120 minutes after pH adjustment | 6200 | 15200 | 8200 | 17500 | 3900 |
| Degree of remaining organic peracid (%) |  |  | 89.9 | 89.4 | 82.0 | 76.4 | 86.7 |

|  |  |  | Products of the invention | | | | |
|---|---|---|---|---|---|---|---|
|  |  |  | 1-6 | 1-7 | 1-8 | 1-9 | 1-10 |
| Compounding component | (A) | Ethylene glycol monoacetate |  |  | 3 g (0.0288) |  |  |
|  |  | Ethylene glycol diacetate |  |  |  | 3 g (0.0205) |  |
|  |  | Diacetin |  |  |  |  | 3 g (0.0170) |
|  |  | Triacetin |  |  |  |  |  |
|  |  | Pentaerythritol tetraacetate |  |  |  |  |  |
|  |  | Pentaacetyl-β-D-glucose | 2 g (0.0051) |  |  |  |  |
|  |  | Glycerine fatty acid ester |  | 2 g (0.0092) |  |  |  |
|  | (B) | Aqueous hydrogen peroxide (35 wt %) | 2.86 g (0.0294) | 2.86 g (0.0294) | 2.86 g (0.0294) | 2.86 g (0.0294) | 2.86 g (0.0294) |
|  |  | Sodium percarbonate |  |  |  |  |  |
|  |  | Sodium perborate |  |  |  |  |  |
| (A)/(B) molar ratio |  |  | 0.17 | 0.31 | 0.98 | 0.70 | 0.58 |
| pH(25° C.) |  |  | 4.0 | 4.0 | 4.9 | 4.9 | 4.9 |
| Organic peracid concentration (ppm) |  | Just after pH adjustment | 25800 | 2700 | 9800 | 21500 | 16100 |
|  |  | 30 minutes after pH adjustment | 24100 | 2700 | 9600 | 21000 | 15700 |
|  |  | 60 minutes after pH adjustment | 22000 | 2500 | 9300 | 19800 | 14200 |
|  |  | 120 minutes after pH adjustment | 19800 | 2000 | 9000 | 18400 | 12300 |
| Degree of remaining organic peracid (%) |  |  | 76.7 | 74.1 | 91.8 | 85.6 | 76.4 |

Notes: The numerical value in the parentheses in the compounding ingredient is the number of moles, and the number of moles in the parentheses in the component (B) is the number of moles in terms of hydrogen peroxide (this applies hereinafter). The (A)/(B) molar ratio is the molar ratio of the component (A) to hydrogen peroxide (this applies hereinafter). The degree of remaining organic peracid is calculated from (organic peracid concentration just after pH adjustment)/(organic peracid concentration 120 minutes after pH adjustment)×100 (this applies hereinafter). Among the components (A), the fatty acid in the glycerin fatty ester [trade name: Homotex PT, manufactured by Kao Corporation] is a C8 fatty acid (this applies hereinafter). The sodium percarbonate contained 22 wt % hydrogen peroxide, and the sodium perborate contained 20 wt % hydrogen peroxide.

TABLE 2

|  |  |  | Products of the invention | | | | |
|---|---|---|---|---|---|---|---|
|  |  |  | 1-11 | 1-12 | 1-13 | 1-14 | 1-15 |
| Compounding component | (A) | Ethylene glycol monoacetate |  |  |  |  | 5 g (0.0481) |
|  |  | Ethylene glycol diacetate |  |  |  |  |  |
|  |  | Diacetin |  |  |  |  |  |
|  |  | Triacetin | 3 g (0.0138) |  |  |  |  |
|  |  | Pentaerythritol tetraacetate |  | 3 g (0.0099) |  |  |  |
|  |  | Pentaacetyl-β-D-glucose |  |  | 3 g (0.0077) |  |  |
|  |  | Glycerine fatty acid ester |  |  |  | 3 g (0.0138) |  |
|  | (B) | Aqueous hydrogen peroxide (35 wt %) | 2.86 g (0.0294) | 2.86 g (0.0294) | 2.86 g (0.0294) | 2.86 g (0.0294) | 2.86 g (0.0294) |
|  |  | Sodium percarbonate |  |  |  |  |  |
|  |  | Sodium perborate |  |  |  |  |  |
| (A)/(B) molar ratio |  |  | 0.47 | 0.34 | 0.26 | 0.47 | 1.64 |
| pH(25° C.) |  |  | 4.9 | 4.9 | 4.9 | 4.9 | 3.8 |

TABLE 2-continued

| | | | | | | |
|---|---|---|---|---|---|---|
| Organic peracid concentration (ppm) | Just after pH adjustment | 25400 | 6800 | 28700 | 4100 | 12300 |
| | 30 minutes after pH adjustment | 24300 | 6100 | 27400 | 3900 | 11700 |
| | 60 minutes after pH adjustment | 23600 | 5700 | 26800 | 3700 | 10500 |
| | 120 minutes after pH adjustment | 20500 | 5000 | 24900 | 3500 | 10000 |
| Degree of remaining organic peracid (%) | | 80.7 | 73.5 | 86.8 | 85.4 | 81.3 |

| | | Product of the invention | | | | |
|---|---|---|---|---|---|---|
| | | 1-16 | 1-17 | 1-18 | 1-19 | 1-20 |
| Compounding component | (A) Ethylene glycol monoacetate | | | | | |
| | Ethylene glycol diacetate | 5 g (0.0342) | | | | |
| | Diacetin | | 5 g (0.0284) | | | |
| | Triacetin | | | 5 g (0.0229) | | |
| | Pentaerythritol tetraacetate | | | | 5 g (0.0164) | |
| | Pentaacetyl-β-D-glucose | | | | | 5 g (0.0128) |
| | Glycerine fatty acid ester | | | | | |
| | (B) Aqueous hydrogen peroxide (35 wt %) | 2.86 g (0.0294) | 2.86 g (0.0294) | 2.86 g (0.0294) | 2.86 g (0.0294) | 2.86 g (0.0294) |
| | Sodium percarbonate | | | | | |
| | Sodium perborate | | | | | |
| (A)/(B) molar ratio | | 1.16 | 0.97 | 0.78 | 0.56 | 0.44 |
| pH(25° C.) | | 3.8 | 3.8 | 3.8 | 3.8 | 3.8 |
| Organic peracid concentration (ppm) | Just after pH adjustment | 22000 | 23200 | 31700 | 9300 | 33500 |
| | 30 minutes after pH adjustment | 20500 | 22200 | 29900 | 8600 | 32000 |
| | 60 minutes after pH adjustment | 18800 | 21000 | 27600 | 7800 | 30600 |
| | 120 minutes after pH adjustment | 17800 | 20300 | 25800 | 7200 | 28100 |
| Degree of remaining organic peracid (%) | | 80.9 | 87.5 | 81.4 | 77.4 | 83.9 |

TABLE 3

| | | Products of the invention | | | | |
|---|---|---|---|---|---|---|
| | | 1-21 | 1-22 | 1-23 | 1-24 | 1-25 |
| Compounding component | (A) Ethylene glycol monoacetate | 2 g (0.0192) | | | | |
| | Ethylene glycol diacetate | | 2 g (0.0137) | | | |
| | Diacetin | | | 2 g (0.0114) | | |
| | Triacetin | | | | 2 g (0.0092) | |
| | Pentaerythritol tetraacetate | | | | | 2 g (0.0066) |
| | Pentaacetyl-β-D-glucose | | | | | |
| | Glycerine fatty acid ester | | | | | |
| | (B) Aqueous hydrogen peroxide (35 wt %) | | | | | |
| | Sodium hydrogen percarbonate | 4.55 g (0.0294) | 4.55 g (0.0294) | 4.55 g (0.0294) | 4.55 g (0.0294) | 4.55 g (0.0294) |
| | Sodium perborate | | | | | |
| (A)/(B) molar ratio | | 0.65 | 0.47 | 0.39 | 0.31 | 0.22 |
| pH(25° C.) | | 4.2 | 4.2 | 4.2 | 4.2 | 4.2 |
| Organic peracid concentration (ppm) | Just after pH adjustment | 7000 | 17500 | 11500 | 23100 | 4600 |
| | 30 minutes after pH adjustment | 6900 | 17000 | 9800 | 21500 | 4400 |
| | 60 minutes after pH adjustment | 6800 | 16200 | 9300 | 19800 | 4300 |
| | 120 minutes after pH adjustment | 6200 | 15000 | 8500 | 18600 | 3800 |
| Degree of remaining organic peracid (%) | | 88.6 | 85.7 | 73.9 | 80.5 | 82.6 |

| | | Products of the invention | | | | |
|---|---|---|---|---|---|---|
| | | 1-26 | 1-27 | 1-28 | 1-29 | 1-30 |
| Compounding component | (A) Ethylene glycol monoacetate | | | | | |
| | Ethylene glycol diacetate | | | 3 g (0.0205) | | |
| | Diacetin | | | | | |
| | Triacetin | | | | 3 g (0.0138) | |

TABLE 3-continued

|  |  |  |  |  |  |  |
|---|---|---|---|---|---|---|
|  | Pentaerythritol tetraacetate |  |  |  |  |  |
|  | Pentaacetyl-β-D-glucose | 2 g (0.0051) |  |  |  | 3 g (0.0077) |
|  | Glycerine fatty acid ester |  | 2 g (0.0092) |  |  |  |
| (B) | Aqueous hydrogen peroxide (35 wt %) |  |  |  |  |  |
|  | Sodium hydrogen percarbonate | 4.55 g (0.0294) | 4.55 g (0.0294) |  |  |  |
|  | Sodium perborate |  |  | 5.00 g (0.0294) | 5.00 g (0.0294) | 5.00 g (0.0294) |
| (A)/(B) molar ratio |  | 0.17 | 0.31 | 0.70 | 0.47 | 0.26 |
| pH(25° C.) |  | 4.2 | 4.2 | 4.5 | 4.5 | 4.5 |
| Organic peracid concentration (ppm) | Just after pH adjustment | 26200 | 2900 | 23000 | 23600 | 26700 |
|  | 30 minutes after pH adjustment | 25100 | 2800 | 21600 | 21500 | 24300 |
|  | 60 minutes after pH adjustment | 22500 | 2600 | 20100 | 19700 | 23900 |
|  | 120 minutes after pH adjustment | 20000 | 2200 | 19200 | 18300 | 21300 |
| Degree of remaining organic peracid (%) |  | 76.3 | 75.9 | 83.5 | 77.5 | 79.8 |

TABLE 4

|  |  | Comparative product ||||| 
|---|---|---|---|---|---|---|
|  |  | 1-1 | 1-2 | 1-3 | 1-4 | 1-5 |
| Compounding component | (A) Ethylene glycol monoacetate | 0.2 g (0.0019) |  |  |  |  |
|  | Ethylene glycol diacetate |  |  |  |  | 2 g (0.0137) |
|  | Diacetin |  | 0.2 g (0.0011) |  |  |  |
|  | Triacetin |  |  | 0.2 g (0.0009) |  |  |
|  | Pentaerythritol tetraacetate |  |  |  | 0.2 g (0.0007) |  |
|  | Pentaacetyl-β-D-glucose |  |  |  |  |  |
|  | Glycerine fatty acid ester |  |  |  |  |  |
|  | (B) Aqueous hydrogen peroxide (35 wt %) | 2.86 g (0.0294) | 2.86 g (0.0294) | 2.86 g (0.0294) | 2.86 g (0.0294) | 2.86 g (0.0294) |
|  | Sodium percarbonate |  |  |  |  |  |
|  | Sodium perborate |  |  |  |  |  |
| (A)/(B) molar ratio |  | 0.06 | 0.04 | 0.03 | 0.02 | 0.47 |
| pH(25° C.) |  | 4.0 | 4.0 | 4.0 | 4.0 | 9.5 |
| Organic peracid concentration (ppm) | Just after pH adjustment | <1000 | <1000 | 1600 | <1000 | 17000 |
|  | 30 minutes after pH adjustment | <1000 | <1000 | <1000 | <1000 | 15100 |
|  | 60 minutes after pH adjustment | <1000 | <1000 | <1000 | <1000 | 10100 |
|  | 120 minutes after pH adjustment | <1000 | <1000 | <1000 | <1000 | 5600 |
| Degree of remaining organic peracid (%) |  | — | — | — | — | 32.9 |

|  |  | Comparative product ||||| 
|---|---|---|---|---|---|---|
|  |  | 1-6 | 1-7 | 1-8 | 1-9 | 1-10 |
| Compounding component | (A) Ethylene glycol monoacetate |  |  |  |  |  |
|  | Ethylene glycol diacetate |  |  |  |  |  |
|  | Diacetin | 2 g (0.0114) |  |  |  |  |
|  | Triacetin |  | 2 g (0.0092) |  |  |  |
|  | Pentaerythritol tetraacetate |  |  | 3 g (0.0099) |  |  |
|  | Pentaacetyl-β-D-glucose |  |  |  | 3 g (0.0077) |  |
|  | Glycerine fatty acid ester |  |  |  |  | 3 g (0.0138) |
|  | (B) Aqueous hydrogen peroxide (35 wt %) | 2.86 g (0.0294) | 2.86 g (0.0294) | 2.86 g (0.0294) | 2.86 g (0.0294) | 2.86 g (0.0294) |
|  | Sodium percarbonate |  |  |  |  |  |
|  | Sodium perborate |  |  |  |  |  |
| (A)/(B) molar ratio |  | 0.39 | 0.31 | 0.34 | 0.26 | 0.47 |
| pH(25° C.) |  | 9.5 | 9.5 | 9.5 | 9.5 | 9.5 |
| Organic peracid concentration (ppm) | Just after pH adjustment | 10000 | 22900 | 6800 | 28700 | 4100 |
|  | 30 minutes after pH adjustment | 8500 | 15600 | 4800 | 21400 | 3200 |
|  | 60 minutes after pH adjustment | 6200 | 11000 | 3600 | 16300 | 2700 |
|  | 120 minutes after pH adjustment | 4300 | 4200 | 1300 | 10300 | 1600 |
| Degree of remaining organic peracid (%) |  | 43.0 | 18.3 | 19.1 | 35.9 | 39.0 |

TABLE 5

| | | | Comparative product | | | | |
|---|---|---|---|---|---|---|---|
| | | | 1-11 | 1-12 | 1-13 | 1-14 | 1-15 |
| Compounding component | (A) | Ethylene glycol monoacetate | 0.2 g (0.0019) | | | | |
| | | Ethylene glycol diacetate | | | | | 2 g (0.0137) |
| | | Diacetin | | 0.2 g (0.0011) | | | |
| | | Triacetin | | | 0.2 g (0.0009) | | |
| | | Pentaerythritol tetraacetate | | | | 0.2 g (0.0007) | |
| | | Pentaacetyl-β-D-glucose | | | | | |
| | | Glycerine fatty acid ester | | | | | |
| | (B) | Aqueous hydrogen peroxide (35 wt %) | | | | | |
| | | Sodium percarbonate | 4.55 g (0.0294) | 4.55 g (0.0294) | | | 4.55 g (0.0294) |
| | | Sodium perborate | | | 5.00 g (0.0294) | 5.00 g (0.0294) | |
| (A)/(B) molar ratio | | | 0.06 | 0.04 | 0.03 | 0.02 | 0.47 |
| pH(25° C.) | | | 4.0 | 4.0 | 4.2 | 4.2 | 9.2 |
| Organic peracid concentration (ppm) | | Just after pH adjustment | <1000 | <1000 | 1500 | <1000 | 17500 |
| | | 30 minutes after pH adjustment | <1000 | <1000 | 1000 | <1000 | 15500 |
| | | 60 minutes after pH adjustment | <1000 | <1000 | <1000 | <1000 | 11000 |
| | | 120 minutes after pH adjustment | <1000 | <1000 | <1000 | <1000 | 5700 |
| Degree of remaining organic peracid (%) | | | — | — | — | — | 32.6 |

| | | | Comparative product | | | | |
|---|---|---|---|---|---|---|---|
| | | | 1-16 | 1-17 | 1-18 | 1-19 | 1-20 |
| Compounding component | (A) | Ethylene glycol monoacetate | | | | | |
| | | Ethylene glycol diacetate | | | | | |
| | | Diacetin | 2 g (0.0114) | | | | |
| | | Triacetin | | 2 g (0.0092) | 3 g (0.0138) | | |
| | | Pentaerythritol tetraacetate | | | | 3 g (0.0099) | |
| | | Pentaacetyl-β-D-glucose | | | | | 3 g (0.0077) |
| | | Glycerine fatty acid ester | | | | | |
| | (B) | Aqueous hydrogen peroxide (35 wt %) | | | | | |
| | | Sodium percarbonate | 4.55 g (0.0294) | 4.55 g (0.0294) | | | |
| | | Sodium perborate | | | 5.00 g (0.0294) | 5.00 g (0.0294) | 5.00 g (0.0294) |
| (A)/(B) molar ratio | | | 0.39 | 0.31 | 0.47 | 0.34 | 0.26 |
| pH(25° C.) | | | 9.2 | 9.2 | 9.0 | 9.0 | 9.0 |
| Organic peracid concentration (ppm) | | Just after pH adjustment | 11500 | 23100 | 23600 | 7000 | 26700 |
| | | 30 minutes after pH adjustment | 9100 | 15700 | 15200 | 5000 | 21000 |
| | | 60 minutes after pH adjustment | 8300 | 11100 | 10500 | 3500 | 15900 |
| | | 120 minutes after pH adjustment | 4600 | 4700 | 4300 | 1200 | 10100 |
| Degree of remaining organic peracid (%) | | | 40.0 | 20.3 | 18.2 | 17.1 | 37.8 |

EXAMPLE 2

The components (A) and (B) in the amounts shown in Tables 6 to 9, 50 g deionized water and a suitable amount of an alkaline pH adjusting agent [sodium carbonate] were mixed for 20 minutes with stirring in a 200 mL beaker. The pH value in this step was controlled in the range of 8 to 12. Thereafter, the mixture was adjusted to the objective pH value by using an acidic pH adjusting agent [citric acid] to give a sterilizer composition. The resulting sterilizer composition was used to measure a sterilizing effect by the following method. The results are shown in Tables 6 to 9.

(1) Sterilizing Effect of Microbial Spores

Spore-forming microorganisms *Bacillus subtilis* var. *niger* and *Bacillus circulans* IFO3967 were pre-cultured respectively in SCD agar mediums (manufactured by Nihon Pharmaceutical Co., Ltd.) at 30° C. for about 4 weeks, and a suitable amount of colonies formed on the agar medium was scratched away, suspended in 1 mL distilled water, and examined under a microscope to confirm the formation of microbial spores (referred to hereinafter as "spores"). This suspension was washed twice by centrifuge and then adjusted with a suitable amount of distilled water to a microbial density of about $10^8$ to $10^9$ cells/mL (spore suspension 1). 0.1 ml of the spore suspension 1 was put into 2 mL of each of the sterilizer compositions in Tables 6 to 9, to allow the composition to act thereon at 25° C. for 120 seconds. Immediately thereafter, 0.1 mL of the sterilizer composition containing the spore suspension 1 was added to an SCDLP medium (manufactured by Nihon Pharmaceutical Co., Ltd.) containing 1.0% sodium thiosulfate to inactivate the sterilizer composition (spore suspension 2). 0.2 mL of the spore suspension 2 was spread on a standard agar medium of 9 cm in diameter and cultured at 35° C. for 36 hours, and the number of colonies formed on the medium was counted to confirm the number of remaining bacteria.

(2) Sterilizing Effect of Fungal Spores

*Aspergillus niger* IFO6341 was pre-cultured in a potato dextrose agar medium (manufactured by Nihon Pharmaceutical Co., Ltd.) at 25° C. for about 4 weeks. Fungi formed on the medium were scratched away and suspended in 5 mL distilled water, and the fungal suspension was made uniform by a glass homogenizer. This suspension was washed twice by centrifuge and then adjusted with a suitable amount of distilled water to a microbial density of about $10^8$ to $10^9$ cells/mL (spore suspension 1). 0.1 ml of the spore suspension 1 was put into 2 mL of each of the sterilizer compositions in Tables 6 to 9, to allow the composition to act thereon at 25° C. for 120 seconds. Immediately thereafter, 0.1 mL of the sterilizer composition containing the spore suspension 1 was added to an SCDLP medium (manufactured by Nihon Pharmaceutical Co., Ltd.) containing 1.0% sodium thiosulfate to inactivate the sterilizer composition (spore suspension 2). 0.2 mL of the spore suspension 2 was spread on a potato dextrose agar medium of 9 cm in diameter and cultured at 25° C. for 3 to 4 days, and the number of colonies formed on the medium was counted to confirm

TABLE 6

| | | | Product of the invention | | | | |
|---|---|---|---|---|---|---|---|
| | | | 2-1 | 2-2 | 2-3 | 2-4 | 2-5 |
| Compounding ingredients | (A) | Ethylene glycol monoacetate | 2 g (0.0192) | | | | |
| | | Ethylene glycol diacetate | | 2 g (0.0137) | | | |
| | | Diacetin | | | 2 g (0.0114) | | |
| | | Triacetin | | | | 2 g (0.0092) | |
| | | Pentaerythritol tetraacetate | | | | | 5 g (0.0164) |
| | | Pentaacetyl-β-D-glucose | | | | | |
| | | Glycerine fatty acid ester | | | | | |
| | (B) | Aqueous hydrogen peracid (35 wt % | 2.86 g (0.0294) | 2.86 g (0.0294) | 2.86 g (0.0294) | 2.86 g (0.0294) | 2.86 g (0.0294) |
| | | Sodium percarbonate | | | | | |
| | | Sodium perborate | | | | | |
| (A)/(B) molar ratio | | | 0.65 | 0.47 | 0.39 | 0.31 | 0.56 |
| pH(25° C.) | | | 4.0 | 4.0 | 4.0 | 4.0 | 4.0 |
| Organic peracid concentration (ppm) | | | 5000 | 5000 | 4000 | 4000 | 4000 |
| Number of remaining microorganisms (CFU/mL) | | *Bacillus subtilis* | <50 | <50 | <50 | <50 | <50 |
| | | *Bacillus circulans* | <50 | <50 | <50 | <50 | <50 |
| | | *Aspergillus niger* | <50 | <50 | <50 | <50 | <50 |

| | | | Product of the invention | | | | |
|---|---|---|---|---|---|---|---|
| | | | 2-6 | 2-7 | 2-8 | 2-9 | 2-10 |
| Compounding ingredients | (A) | Ethylene glycol monoacetate | | | 3 g (0.0288) | | |
| | | Ethylene glycol diacetate | | | | | |
| | | Diacetin | | | | | |
| | | Triacetin | | | | 5 g (0.0229) | |
| | | Pentaerythritol tetraacetate | | | | | |
| | | Pentaacetyl-β-D-glucose | 2 g (0.0051) | | | | 5 g (0.0128) |
| | | Glycerine fatty acid ester | | 5 g (0.0229) | | | |
| | (B) | Aqueous hydrogen peracid (35 wt % | 2.86 g (0.0294) | 2.86 g (0.0294) | 2.86 g (0.0294) | 2.86 g (0.0294) | 2.86 g (0.0294) |
| | | Sodium percarbonate | | | | | |
| | | Sodium perborate | | | | | |
| (A)/(B) molar ratio | | | 0.17 | 0.78 | 0.98 | 0.78 | 0.44 |
| pH(25° C.) | | | 4.0 | 4.0 | 4.9 | 3.8 | 3.8 |
| Organic peracid concentration (ppm) | | | 4000 | 4000 | 4000 | 4000 | 4000 |
| Number of remaining microorganisms (CFU/mL) | | *Bacillus subtilis* | <50 | 150 | <50 | <50 | <50 |
| | | *Bacillus circulans* | <50 | 200 | <50 | <50 | <50 |
| | | *Aspergillus niger* | <50 | 150 | <50 | <50 | <50 |

TABLE 7

|  |  | Product of the invention | | | | |
|---|---|---|---|---|---|---|
|  |  | 2-11 | 2-12 | 2-13 | 2-14 | 2-15 |
| Compounding ingredients | (A) Ethylene glycol monoacetate | 2 g (0.0192) |  |  |  |  |
|  | Ethylene glycol diacetate |  | 2 g (0.0137) |  |  |  |
|  | Diacetin |  |  | 2 g (0.0114) |  |  |
|  | Triacetin |  |  |  | 2 g (0.0092) |  |
|  | Pentaerythritom tetraacetate |  |  |  |  | 5 g (0.0164) |
|  | Pentaacetyl-β-D-glucose |  |  |  |  |  |
|  | Glycerine fatty acid ester |  |  |  |  |  |
|  | (B) Aqueous hydrogen peroxide (35 wt %) |  |  |  |  |  |
|  | Sodium percarbonate | 4.55 g (0.0294) | 4.55 g (0.0294) | 4.55 g (0.0294) | 4.55 g (0.0294) | 4.55 g (0.0294) |
|  | Sodium perborate |  |  |  |  |  |
| (A)/(B) molar ratio |  | 0.65 | 0.47 | 0.39 | 0.31 | 0.56 |
| pH(25° C.) |  | 4.2 | 4.2 | 4.2 | 4.2 | 3.9 |
| Organic peracid concentration (ppm) |  | 4000 | 4000 | 4000 | 4000 | 4000 |
| Number of remaining microorganisms (CFU/mL) | Bacillus subtilis | <50 | <50 | <50 | <50 | <50 |
|  | Bacillus circulans | <50 | <50 | <50 | <50 | <50 |
|  | Aspergillus niger | <50 | <50 | <50 | <50 | <50 |

|  |  | Product of the invention | | | | |
|---|---|---|---|---|---|---|
|  |  | 2-16 | 2-17 | 2-18 | 2-19 | 2-20 |
| Compounding ingredients | (A) Ethylene glycol monoacetate |  |  | 3 g (0.0288) |  |  |
|  | Ethylene glycol diacetate |  |  |  |  |  |
|  | Diacetin |  |  |  |  |  |
|  | Triacetin |  |  |  | 5 g (0.0229) |  |
|  | Pentaerythritol tetraacetate |  |  |  |  |  |
|  | Pentaacetyl-β-D-glucose | 2 g (0.0051) |  |  |  | 5 g (0.0128) |
|  | Glycerine fatty acid ester |  | 5 g (0.0229) |  |  |  |
|  | (B) Aqueous hydrogen peracid (35 wt % |  |  |  |  |  |
|  | Sodium percarbonate | 4.55 g (0.0294) | 4.55 g (0.0294) |  |  |  |
|  | Sodium perborate |  |  | 5.00 g (0.0294) | 5.00 g (0.0294) | 5.00 g (0.0294) |
| (A)/(B) molar ratio |  | 0.17 | 0.78 | 0.98 | 0.78 | 0.44 |
| pH(25° C.) |  | 4.2 | 3.9 | 4.5 | 3.9 | 3.9 |
| Organic peracid concentration (ppm) |  | 4000 | 4000 | 4000 | 4000 | 4000 |
| Number of remaining microorganisms (CFU/mL) | Bacillus subtilis | <50 | 200 | <50 | <50 | <50 |
|  | Bacillus circulans | <50 | 200 | <50 | <50 | <50 |
|  | Aspergillus niger | <50 | 250 | <50 | <50 | <50 |

TABLE 8

|  |  | Comparative product | | | | |
|---|---|---|---|---|---|---|
|  |  | 2-1 | 2-2 | 2-3 | 2-4 | 2-5 |
| Compounding components | (A) Ethylene glycol monoacetate | 2 g (0.0192) |  |  |  |  |
|  | Ethylene glycol diacetate |  |  |  |  | 2 g (0.0137) |
|  | Diacetin |  | 2 g (0.0114) |  |  |  |
|  | Triacetin |  |  | 2 g (0.0092) |  |  |
|  | Pentaerythritom tetraacetate |  |  |  | 2 g (0.0066) |  |
|  | Pentaacetyl-β-D-glucose |  |  |  |  |  |
|  | Glycerine fatty acid ester |  |  |  |  |  |

TABLE 8-continued

|  |  |  | | | | | |
|---|---|---|---|---|---|---|---|
| | (B) | Aqueous hydrogen peroxide (35 wt %) | 2.86 g (0.0294) | 2.86 g (0.0294) | 2.86 g (0.0294) | 2.86 g (0.0294) | 2.86 g (0.0294) |
| | | Sodium percarbonate | | | | | |
| | | Sodium perborate | | | | | |
| (A)/(B) molar ratio | | | 0.65 | 0.39 | 0.31 | 0.22 | 0.47 |
| pH(25° C.) | | | 7.8 | 7.8 | 7.8 | 7.8 | 9.5 |
| Organic peracid concentration(ppm) | | | 5000 | 5000 | 4000 | 4000 | 4000 |
| Number of remaining | | Bacillus subtilis | $2.3 \times 10^5$ | $2.8 \times 10^5$ | $8.5 \times 10^6$ | $6.8 \times 10^6$ | $3.2 \times 10^7$ |
| microorganisms | | Bacillus circulans | $6.2 \times 10^5$ | $5.6 \times 10^5$ | $1.3 \times 10^7$ | $1.9 \times 10^7$ | $3.0 \times 10^7$ |
| (CFU/mL) | | Aspergillus niger | $5.6 \times 10^4$ | $1.0 \times 10^5$ | $5.9 \times 10^5$ | $8.3 \times 10^5$ | $8.1 \times 10^7$ |

| | | | Comparative product | | | | |
|---|---|---|---|---|---|---|---|
| | | | 2-6 | 2-7 | 2-8 | 2-9 | 2-10 |
| Compounding components | (A) | Ethylene glycol monoacetate | | | | | |
| | | Ethylene glycol diacetate | | | | | |
| | | Diacetin | 2 g (0.0114) | | | | |
| | | Triacetin | | 2 g (0.0092) | | | |
| | | Pentaerythritom tetraacetate | | | 3 g (0.0099) | | |
| | | Pentaacetyl-β-D-glucose | | | | 3 g (0.0077) | |
| | | Glycerine fatty acid ester | | | | | 3 g (0.0138) |
| | (B) | Aqueous hydrogen peroxide (35 wt %) | 2.86 g (0.0294) | 2.86 g (0.0294) | 2.86 g (0.0294) | 2.86 g (0.0294) | 2.86 g (0.0294) |
| | | Sodium percarbonate | | | | | |
| | | Sodium perborate | | | | | |
| (A)/(B) molar ratio | | | 0.39 | 0.31 | 0.34 | 0.26 | 0.47 |
| pH(25° C.) | | | 9.5 | 9.5 | 9.5 | 9.5 | 9.5 |
| Organic peracid concentration(ppm) | | | 4000 | 4000 | 4000 | 4000 | 4000 |
| Number of remaining | | Bacillus subtilis | $2.9 \times 10^7$ | $2.5 \times 10^7$ | $3.8 \times 10^7$ | $2.1 \times 10^7$ | $3.3 \times 10^7$ |
| microorganisms | | Bacillus circulans | $2.6 \times 10^7$ | $1.5 \times 10^7$ | $2.1 \times 10^7$ | $2.3 \times 10^7$ | $2.1 \times 10^7$ |
| (CFU/mL) | | Aspergillus niger | $7.1 \times 10^7$ | $7.5 \times 10^7$ | $7.7 \times 10^7$ | $7.5 \times 10^7$ | $8.0 \times 10^7$ |

TABLE 9

| | | | Comparative product | | | | |
|---|---|---|---|---|---|---|---|
| | | | 2-11 | 2-12 | 2-13 | 2-14 | 2-15 |
| Compounding components | (A) | Ethylene glycol monoacetate | 2 g (0.0192) | | | | |
| | | Ethylene glycol diacetate | | | | | 2 g (0.0137) |
| | | Diacetin | | 2 g (0.0114) | | | |
| | | Triacetin | | | 2 g (0.0092) | | |
| | | Pentaerythritom tetraacetate | | | | 2 g (0.0066) | |
| | | Pentaacetyl-β-D-glucose | | | | | |
| | | Glycerine fatty acid ester | | | | | |
| | (B) | Aqueous hydrogen peroxide (35 wt %) | | | | | |
| | | Sodium percarbonate | 455 g (0.0294) | 455 g (0.0294) | | | 455 g (0.0294) |
| | | Sodium perborate | | | 5.00 (0.0294) | 5.00 (0.0294) | |
| (A)/(B) molar ratio | | | 0.65 | 0.39 | 0.31 | 0.22 | 0.47 |
| pH(25° C.) | | | 7.8 | 7.8 | 7.9 | 7.9 | 9.2 |
| Organic peracid concentration(ppm) | | | 4000 | 4000 | 4000 | 4000 | 4000 |
| Number of remaining | | Bacillus subtilis | $2.1 \times 10^5$ | $2.5 \times 10^5$ | $1.2 \times 10^5$ | $5.6 \times 10^5$ | $6.2 \times 10^7$ |
| microorganisms | | Bacillus circulans | $6.1 \times 10^5$ | $5.9 \times 10^5$ | $6.9 \times 10^5$ | $5.9 \times 10^5$ | $3.6 \times 10^7$ |
| (CFU/mL) | | Aspergillus niger | $7.3 \times 10^4$ | $7.6 \times 10^5$ | $5.8 \times 10^5$ | $6.1 \times 10^5$ | $6.9 \times 10^7$ |

TABLE 9-continued

|  |  |  | Comparative product | | | | |
|---|---|---|---|---|---|---|---|
|  |  |  | 2-16 | 2-17 | 2-18 | 2-19 | 2-20 |
| Compounding components | (A) | Ethylene glycol monoacetate | | | | | |
|  |  | Ethylene glycol diacetate | | | | | |
|  |  | Diacetin | 2 g (0.0114) | | | | |
|  |  | Triacetin | | 2 g (0.0092) | | | |
|  |  | Pentaerythritom tetraacetate | | | 3 g (0.0092) | | |
|  |  | Pentaacetyl-β-D-glucose | | | | 3 g (0.0077) | |
|  |  | Glycerine fatty acid ester | | | | | 3 g (0.0138) |
|  | (B) | Aqueous hydrogen peroxide (35 wt %) | | | | | |
|  |  | Sodium percarbonate | 455 g (0.0294) | 455 g (0.0294) | | | |
|  |  | Sodium perborate | | | 5.00 g (0.0294) | 5.00 g (0.0294) | 5.00 g (0.0294) |
| (A)/(B) molar ratio | | | 0.39 | 0.31 | 0.34 | 0.26 | 0.47 |
| pH(25° C.) | | | 9.2 | 9.2 | 9.0 | 9.0 | 9.0 |
| Organic peracid concentration(ppm) | | | 4000 | 4000 | 4000 | 4000 | 4000 |
| Number of remaining microorganisms (CFU/mL) | | Bacillus subtilis | $5.4 \times 10^7$ | $4.9 \times 10^7$ | $5.6 \times 10^7$ | $6.2 \times 10^7$ | $6.8 \times 10^7$ |
|  |  | Bacillus circulans | $2.8 \times 10^7$ | $3.0 \times 10^7$ | $3.9 \times 10^7$ | $3.2 \times 10^7$ | $3.2 \times 10^7$ |
|  |  | Aspergillus niger | $7.6 \times 10^7$ | $7.6 \times 10^7$ | $7.4 \times 10^7$ | $7.5 \times 10^7$ | $8.6 \times 10^7$ |

EXAMPLE 3

Deionized water was added to the components (A) and (B), organic phosphonic acid (trade name: Dequest 2010, manufactured by Solutia Japan Ltd.) and an alkaline pH adjusting agent in the amounts shown in Table 10, to adjust the total weight of the mixture to 100 g. This mixture was mixed with stirring for about 10 minutes in a 200 mL beaker. The pH in this step was 8 to 12. Thereafter, the mixture was rapidly adjusted to the objective pH by using an acidic pH adjusting agent in a weight shown in Table 10, followed by adding deionized water to adjust the total amount to 110 g. At this point in time (just after preparation), the mixture was measured for organic peracid concentration and hydrogen peroxide concentration, and about 30 minutes after the stirring, the aqueous solution for sterilization was adjusted to an organic peracid concentration of 3000 ppm, and its sterilizing effect was confirmed. The method of measuring the hydrogen peroxide concentration and the organic peracid concentration was conducted according to the method of measuring the organic peracid concentration in Example 1. The sterilization test method was in accordance with measurement of sterilizing effect of bacterial spores in Example 2, but in this example, the temperature and time for contacting the aqueous solution for sterilization with bacteria were 60° C. and 20 seconds respectively, and as the objective bacteria, *Bacillus cereus* IFO13494 and *Bacillus subtilis* var. *niger* were used. The results are shown in Table 10.

TABLE 10

|  |  |  | Product of the invention | | | | |
|---|---|---|---|---|---|---|---|
|  |  |  | 3-1 | 3-2 | 3-3 | 3-4 | 3-5 |
| Compounding components | (A) | Ethylene glycol diaceatate | 5 g (0.0342) | 5 g (0.0342) | | | |
|  |  | Triacetin | | | 5 g (0.0229) | 5 g (0.0229) | 5 g (0.0229) |
|  |  | Pentaacetyl-β-D-glucose | | | | | |
|  | (B) | Aqueous hydrogen peroxide (35 wt %) | 4.3 g (0.0443) | 4.3 g (0.0443) | 4.3 g (0.0443) | 4.3 g (0.0443) | 4.3 g (0.0443) |
|  | Chelating agent (net content) | Organic phosphonic acid | 0.1 g | 0.1 g | 0.1 g | 0.1 g | 0.1 g |
|  | Alkaline pH adjusting agent (net content) | Soium hydroxide | 2 g | | 2 g | | |
|  |  | Sodium carbonate | | | | 6 g | |
|  |  | Trisodim phosphate | | 4 g | | | 4 g |
|  | Acidic pH adjusting agent | Sulfuric acid (purity 98%) | 2.1 g | 2.1 g | — | — | — |
|  |  | Phosphoric acid (purity 85%) | 0.5 g | 0.5 g | 5.0 g | 5.0 g | 5.0 g |
| (A)/(B) molar ratio | | | 0.77 | 0.77 | 0.52 | 0.52 | 0.52 |
| Organic peracid concentration (ppm) just after preparation | | | 25,000 | 24,000 | 27,000 | 22,000 | 26,000 |
| Hydrogen peroxide concentration(ppm) just after preparation | | | 1,500 | 1,650 | 1,050 | 1,900 | 1,350 |
| pH of aqueous solution for sterilization (25° C.) | | | 3.5 | 2.8 | 3.7 | 1.5 | 3.0 |
| Number of remaining microorganisms (CFU/mL) | | *Bacillus cereus* IFO13494 | <50 | <50 | <50 | <50 | <50 |
|  |  | *Bacillus subtilis* var. *niger* | <50 | <50 | <50 | <50 | <50 |

TABLE 10-continued

|  |  |  | Product of the invention | | | | |
|---|---|---|---|---|---|---|---|
|  |  |  | 3-6 | 3-7 | 3-8 | 3-9 | 3-10 |
| Compounding components | (A) | Ethylene glycol diaceatate | | | | | |
|  |  | Triacetin | 5 g (0.0229) | 5 g (0.0229) | 5 g (0.0229) | | |
|  |  | Pentaacetyl-β-D-glucose | | | | 5 g (0.0128) | 5 g (0.0128) |
|  | (B) | Aqueous hydrogen peroxide (35 wt %) | 4.3 g (0.0443) | 4.3 g (0.0443) | 4.3 g (0.0443) | 4.3 g (0.0443) | 4.3 g (0.0443) |
|  | Chelating agent (net content) | Organic phosphonic acid | 0.1 g | 0.1 g | 0.1 g | 0.1 g | 0.1 g |
|  | Alkaline pH adjusting agent (net content) | Soium hydroxide | 2 g | | | 2 g | |
|  |  | Sodium carbonate | | 6 g | | | |
|  |  | Trisodim phosphate | | | 4 g | | 4 g |
|  | Acidic pH adjusting agent | Sulfuric acid (purity 98%) | 2.1 g | 2.1 g | 2.1 g | 2.1 g | 2.1 g |
|  |  | Phosphoric acid (purity 85%) | 0.5 g | 0.5 g | 0.5 g | 0.5 g | 0.5 g |
| (A)/(B) molar ratio | | | 0.52 | 0.52 | 0.52 | 0.29 | 0.29 |
| Organic peracid concentration (ppm) just after preparation | | | 27,000 | 22,000 | 26,000 | 30,000 | 29,500 |
| Hydrogen peroxide concentration(ppm) just after preparation | | | 1,050 | 1,850 | 1,300 | 900 | 950 |
| pH of aqueous solution for sterilization (25° C.) | | | 3.5 | 1.2 | 2.8 | 3.5 | 2.8 |
| Number of remaining microorganisms (CFU/mL) | | Bacillus cereus IFO13494 | <50 | <50 | <50 | <50 | <50 |
|  |  | Bacillus subtilis var. niger | <50 | <50 | <50 | <50 | <50 |

EXAMPLE 4

A composition for production of a sterilizer having a composition shown in Table 11 was prepared and evaluated for storage stability by the following method. The results are shown in Table 11.

<Storage Stability Test Method>

A 200 ml glass bottle (colorless and transparent) was charged with 150 ml composition for production of a sterilizer, then capped and stored at 50° C. After 4 weeks, the concentration of hydrogen peroxide in the composition was measured according to the method of measuring the organic peracid concentration in Example 1, to determine the hydrogen peroxide concentration after storage. The degree of remaining hydrogen peroxide was determined from the following equation and shown as an indicator of storage stability. As the hydrogen peroxide concentration just after preparation, the concentration in the composition, based on the amount of hydrogen peroxide charged into the composition, can be used.

Degree of remaining hydrogen peroxide(%)=[(hydrogen peroxide concentration after storage)/(hydrogen peroxide concentration just after preparation)]×100

TABLE 11

|  |  |  | Product of the invention | | | | | | |
|---|---|---|---|---|---|---|---|---|---|
|  |  |  | 4-1 | 4-2 | 4-3 | 4-4 | 4-5 | 4-6 | 4-7 |
| Formulation (weight-%) | (A) | Triacetin | 66.7 | | | 50 | | | |
|  |  | Diacetin | | 66.7 | | | 50 | | |
|  |  | Ethylene glycol diacetate | | | 66.7 | | | 50 | |
|  |  | Glycein fatty acid ester<sup>※1</sup> | | | | | | | 50 |
|  | (B) | Hydrogen peroxide | 20 | 20 | 20 | 15 | 15 | 15 | 15 |
|  |  | 1-hydroxyethylidene-1,1-diphosphonic acid<sup>※2</sup> | | | | | | | |
|  |  | NaOH<sup>※3</sup> | | | | | | | |
|  |  | Propylene glycol | | | | 25 | 25 | 25 | 25 |
|  |  | Water | 13.3 | 13.3 | 13.3 | 10 | 10 | 10 | 10 |
|  |  | Total | 100.0 | 100.0 | 100.0 | 100.0 | 100.0 | 100.0 | 100.0 |
| Compounded state (visual check) | | | ○ | ○ | ○ | ○ | ○ | ○ | ○ |
| pH (stock solution, 20° C.) | | | 3.0 | 3.3 | 4.5 | 3.1 | 3.5 | 4.7 | 3.8 |
| Storage stability | Degree of remaining hydrogen peroxide (%) | | 82.6 | 66.6 | 86.5 | 69.6 | 53.6 | 81.2 | 84.1 |

|  |  |  | Product of the invention | | Comparative product | | |
|---|---|---|---|---|---|---|---|
|  |  |  | 4-8 | 4-9 | 4-1 | 4-2 | 4-3 |
| Formulation (weight-%) | (A) | Triacetin | 50 | 50 | 50 | 50 | |
|  |  | Diacetin | | | | | 50 |
|  |  | Ethylene glycol diacetate | | | | | |
|  |  | Glycein fatty acid ester<sup>※1</sup> | | | | | |
|  | (B) | Hydrogen peroxide | 15 | 15 | 15 | 15 | 15 |
|  |  | 1-hydroxyethylidene-1,1-diphosphonic acid<sup>※2</sup> | 0.50 | | | | |

TABLE 11-continued

|  |  |  |  |  |  |
|---|---|---|---|---|---|
| NaOH[X.3] | 0.17 | | | | |
| Propylene glycol | 24 | 15 | | 5 | |
| Water | 10.33 | 20 | 35 | 30 | 35 |
| Total | 100.0 | 100.0 | 100.0 | 100.0 | 100.0 |
| Compounded state (visual check) | ○ | ○ | X[X.4] | ○ | ○ |
| pH (stock solution, 20° C.) | 3.1 | 2.8 | — | 2.9 | 3.4 |
| Storage stability — Degree of remaining hydrogen peroxide (%) | 57.3 | 53.1 | — | 43.5 | 30.4 |

[X.1] Homotex PT(trade name, manufactured by Kao Corporation), an ester of glycerine and C8 fatty acid
[X.2] Dequest 2010 (trade name, manufactured by Solutia Japan Ltd.), 60 wt % active ingredient, 40 wt % water
[X.3] 48 wt % active ingredient, 52 wt % water
[X.4] Separated state

EXAMPLE 5 AND COMPARATIVE EXAMPLE 5

Sterilizer compositions were produced in the same manner as in Example 1 except that the components (A) and (B) and deionized water [in the table, symbol (C) is given] in the amounts shown in Tables 12 to 17 and a suitable amount of an alkaline pH adjusting agent [sodium carbonate] were used. The results are shown in Tables 12 to 17.

The components (A) and (B) and deionized water [in the table, symbol (C) is given] in the amounts shown in Table 18 and a suitable amount of an acidic pH adjusting agent [citric acid] were mixed with stirring for about 20 minutes in a 200 mL beaker. The pH in this step was 3 to 5. In this step, the concentration of an organic peracid was measured, but generation of an organic peracid was not recognized. This example is an example wherein the pH in the first step is 3 to 5, and the second step is not carried out. The results are shown in Table 18.

In the method of measuring the concentration of an organic peracid (1), the quantification of hydrogen peroxide (1-1) and the quantification of an organic peracid (1-2) were carried out in the same manner as in Example 1 provided that $w_1$ is the weight (g) of the organic peracid-containing aqueous solution after the second step, and $w_2$ is the weight (g) of the organic peracid-containing aqueous solution after the second step.

TABLE 12

|  |  |  |  | Example | | | | |
|---|---|---|---|---|---|---|---|---|
|  |  |  |  | 5-1 | 5-2 | 5-3 | 5-4 | 5-5 |
| Manufacturing condition | Charging amounts | (A) | Ethylene glycol diacetate | 2 g (0.0137) | 3 g (0.0205) | 5 g (0.0342) | | |
|  |  |  | Triacetin | | | | 2 g (0.0092) | 3 g (0.0138) |
|  |  |  | Pentaacetyl-β-D-glucose | | | | | |
|  |  |  | Glycerin fatty acid ester | | | | | |
|  |  | (B) | Aqueous hydrogen peroxide (35 wt %) | 2.86 g (0.0294) | 2.86 g (0.0294) | 2.86 g (0.0294) | 2.86 g (0.0294) | 2.86 g (0.0294) |
|  |  |  | Sodium percarbonate | | | | | |
|  |  |  | Sodium perborate | | | | | |
|  |  | (C) | water | 48 g | 48 g | 55 g | 48 g | 48 g |
|  | (A)/(B) molar ratio |  |  | 0.47 | 0.70 | 1.16 | 0.31 | 0.47 |
|  | [(A) + (B)]/(C) ratio by weight |  |  | 0.063 | 0.083 | 0.109 | 0.063 | 0.083 |
|  | pH in second step (25° C.) |  |  | 3.7 | 3.7 | 3.7 | 3.7 | 3.7 |
| Organic peracid concentration (ppm) | just after second step |  |  | 18300 | 22100 | 23600 | 22300 | 26100 |
|  | 30 minutes after second step |  |  | 17500 | 21300 | 21600 | 21000 | 25100 |
|  | 60 minutes after second step |  |  | 16300 | 19800 | 20500 | 19300 | 24300 |
| Degree of remaining organic peracid (%) |  |  |  | 89.1 | 89.6 | 86.9 | 86.5 | 93.1 |
| Degree of remaining hydrogen peroxide (%) |  |  |  | 48.3 | 41.8 | 39.9 | 41.2 | 28.7 |

|  |  |  |  | Example | | | | |
|---|---|---|---|---|---|---|---|---|
|  |  |  |  | 5-6 | 5-7 | 5-8 | 5-9 | 5-10 |
| Manufacturing condition | Charging amounts | (A) | Ethylene glycol diacetate | | | | | |
|  |  |  | Triacetin | 5 g (0.0229) | | | | |
|  |  |  | Pentaacetyl-β-D-glucose | | 2 g (0.0051) | 3 g (0.0077) | | |
|  |  |  | Glycerin fatty acid ester | | | | 5 g (0.0229) | 8 g (0.0367) |
|  |  | (B) | Aqueous hydrogen peroxide (35 wt %) | 2.86 g (0.0294) | 2.86 g (0.0294) | 2.86 g (0.0294) | 0.29 g (0.0030) | 0.29 g (0.0030) |
|  |  |  | Sodium percarbonate | | | | | |
|  |  |  | Sodium perborate | | | | | |
|  |  | (C) | water | 55 g | 48 g | 55 g | 55 g | 60 g |
|  | (A)/(B) molar ratio |  |  | 0.78 | 0.17 | 0.26 | 7.63 | 12.23 |
|  | [(A) + (B)]/(C) ratio by weight |  |  | 0.109 | 0.063 | 0.073 | 0.093 | 0.135 |
|  | pH in second step (25° C.) |  |  | 3.7 | 3.7 | 3.7 | 3.7 | 3.7 |

TABLE 12-continued

| | | | | | | |
|---|---|---|---|---|---|---|
| Organic peracid | just after second step | 33700 | 26900 | 29900 | 4500 | 5500 |
| concentration | 30 minutes after second step | 30200 | 25800 | 27900 | 4200 | 5100 |
| (ppm) | 60 minutes after second step | 28700 | 24600 | 25800 | 4000 | 4800 |
| Degree of remaining organic peracid (%) | | 85.2 | 91.4 | 86.3 | 88.9 | 87.3 |
| Degree of remaining hydrogen peroxide (%) | | 8.1 | 38.2 | 25.3 | 28.7 | 19.9 |

Notes: The numerical value in the parentheses in the compounding ingredient is the number of moles, and the number of moles in the parentheses in the component (B) is the number of moles in terms of hydrogen peroxide (this applies hereinafter). The (A)/(B1) molar ratio is the molar ratio of the component (A) to hydrogen peroxide (this applies hereinafter). The "just after second step" in the item "Organic peracid concentration" is just after the pH of the system became the predetermined value, and the degree of remaining organic peracid is calculated from [(organic peracid concentration just after the second step)/(organic peracid concentration 60 minutes after the second step)]×100 (this applies hereinafter).

The degree of remaining hydrogen peroxide is calculated by determining the total weight of hydrogen peroxide in the system on the basis of the concentration of hydrogen peroxide calculated from the formula (I-1), and then dividing the total weight of hydrogen peroxide by the total weight of initially introduced hydrogen peroxide (this applies hereinafter). Among the components (A), the fatty acid in the glycerin fatty ester [trade name: Homotex PT, manufactured by Kao Corporation] is a C8 fatty acid (this applies hereinafter). The sodium percarbonate contained 22 wt % hydrogen peroxide, and the sodium perborate contained 20 wt % hydrogen peroxide.

TABLE 13

| | | | | | Example | | | | |
|---|---|---|---|---|---|---|---|---|---|
| | | | | | 5-11 | 5-12 | 5-13 | 5-14 | 5-15 |
| Manufacturing conditions | Charging amount | (A) | Ethylene glycol diacetate | | 2 g (0.0137) | 3 g (0.0205) | 5 g (0.0342) | | |
| | | | Triacetin | | | | | 2 g (0.0092) | 3 g (0.0138) |
| | | | Pentaacetyl-β-D-glucose | | | | | | |
| | | | Glycerin fatty acid ester | | | | | | |
| | | (B) | Aqueous hydrogen peroxide (35 wt %) | | 2.86 g (0.0294) | 2.86 g (0.0294) | 2.86 g (0.0294) | 2.86 g (0.0294) | 2.86 g (0.0294) |
| | | | Sodium percarbonate | | | | | | |
| | | | Sodium perborate | | | | | | |
| | | (C) | Water | | 48 g | 48 g | 55 g | 48 g | 48 g |
| | (A)/(B) molar ratio | | | | 0.47 | 0.70 | 1.16 | 0.31 | 0.47 |
| | [(A) + (B)]/(C) ratio by weight | | | | 0.063 | 0.083 | 0.109 | 0.063 | 0.083 |
| | pH in second step (25° C.) | | | | 4.9 | 4.9 | 4.9 | 4.9 | 4.9 |
| Organic peracid | | | Just after second step | | 18300 | 22100 | 23600 | 22300 | 26100 |
| concentration | | | 30 minutes after second step | | 16900 | 20700 | 20700 | 20500 | 23300 |
| (ppm) | | | 60 minutes after second step | | 15800 | 18600 | 19200 | 18400 | 20100 |
| Degree of remaining organic peracid (%) | | | | | 86.9 | 84.2 | 81.4 | 82.5 | 77.0 |
| Degree of remaining hydrogen peroxide (%) | | | | | 47.2 | 40.9 | 39.2 | 40.3 | 23.4 |

| | | | | | Example | | | | |
|---|---|---|---|---|---|---|---|---|---|
| | | | | | 5-16 | 5-17 | 5-18 | 5-19 | 5-20 |
| Manufacturing conditions | Charging amount | (A) | Ethylene glycol diacetate | | | | | | |
| | | | Triacetin | | 5 g (0.0229) | | | | |
| | | | Pentaacetyl-β-D-glucose | | | 2 g (0.0051) | 3 g (0.0077) | | |
| | | | Glycerin fatty acid ester | | | | | 5 g (0.0229) | 8 g (0.0367) |
| | | (B) | Aqueous hydrogen peroxide (35 wt %) | | 2.86 g (0.0294) | 2.86 g (0.0294) | 2.86 g (0.0294) | 0.29 g (0.0030) | 0.29 g (0.0030) |
| | | | Sodium percarbonate | | | | | | |
| | | | Sodium perborate | | | | | | |
| | | (C) | Water | | 55 g | 48 g | 55 g | 55 g | 60 g |
| | (A)/(B) molar ratio | | | | 0.78 | 0.17 | 0.26 | 7.63 | 12.23 |
| | [(A) + (B)]/(C) ratio by weight | | | | 0.109 | 0.063 | 0.073 | 0.093 | 0.135 |
| | pH in second step (25° C.) | | | | 4.9 | 4.9 | 4.9 | 4.9 | 4.9 |
| Organic peracid | | | Just after second step | | 33700 | 26900 | 29900 | 4500 | 5500 |
| concentration | | | 30 minutes after second step | | 29500 | 23800 | 23800 | 4000 | 5100 |
| (ppm) | | | 60 minutes after second step | | 27200 | 22400 | 23900 | 3800 | 4600 |
| Degree of remaining organic peracid (%) | | | | | 80.7 | 83.3 | 79.9 | 84.4 | 86.3 |
| Degree of remaining hydrogen peroxide (%) | | | | | 7.5 | 32.8 | 23.1 | 27.7 | 18.3 |

TABLE 14

|  |  |  |  | Example |  |  |  |  |
|---|---|---|---|---|---|---|---|---|
|  |  |  |  | 5-21 | 5-22 | 5-23 | 5-24 | 5-25 |
| Manufacturing conditions | Charging amounts | (A) | Ethylene glycol diacetate | 2 g (0.0137) | 3 g (0.0205) | 5 g (0.0342) |  |  |
|  |  |  | Triacetin |  |  |  | 2 g (0.0092) | 3 g (0.0138) |
|  |  |  | Pentaacetyl-β-D-glucose |  |  |  |  |  |
|  |  |  | Glycerin fatty acid ester |  |  |  |  |  |
|  |  | (B) | Aqueous hydrogen peroxide (35 wt %) | 4.55 g (0.0294) | 4.55 g (0.0294) | 4.55 g (0.0294) | 4.55 g (0.0294) | 4.55 g (0.0294) |
|  |  |  | Sodium percarbonate |  |  |  |  |  |
|  |  |  | Sodium perborate |  |  |  |  |  |
|  |  | (C) | Water | 55 g | 55 g | 55 g | 55 g | 55 g |
|  | (A)/(B) molar ratio |  |  | 0.47 | 0.70 | 1.16 | 0.31 | 0.47 |
|  | [(A) + (B)]/(C) weight ratio |  |  | 0.055 | 0.073 | 0.109 | 0.055 | 0.073 |
|  | pH in second step (25° C.) |  |  | 4.5 | 4.5 | 4.5 | 4.5 | 4.5 |
| Organic peracid concentration (ppm) | Just after second step |  |  | 18500 | 22000 | 23000 | 22100 | 27300 |
|  | 30 minutes after second step |  |  | 17200 | 21000 | 22300 | 21600 | 25400 |
|  | 60 minutes after second step |  |  | 15800 | 19900 | 21500 | 20900 | 23200 |
| Degree of remaining organic peracid (%) |  |  |  | 85.4 | 90.5 | 93.5 | 94.6 | 85.0 |
| Degree of remaining hydrogen peroxide (%) |  |  |  | 46.2 | 38.6 | 35.6 | 37.2 | 20.8 |

|  |  |  |  | Example |  |  |  |  |
|---|---|---|---|---|---|---|---|---|
|  |  |  |  | 5-26 | 5-27 | 5-28 | 5-29 | 5-30 |
| Manufacturing conditions | Charging amounts | (A) | Ethylene glycol diacetate |  |  |  |  |  |
|  |  |  | Triacetin | 5 g (0.0229) |  |  |  |  |
|  |  |  | Pentaacetyl-β-D-glucose |  | 2 g (0.0051) | 3 g (0.0077) |  |  |
|  |  |  | Glycerin fatty acid ester |  |  |  | 5 g (0.0229) | 8 g (0.0367) |
|  |  | (B) | Aqueous hydrogen peroxide (35 wt %) |  |  |  |  |  |
|  |  |  | Sodium percarbonate | 4.55 g (0.0294) |  |  |  |  |
|  |  |  | Sodium perborate |  | 5.00 g (0.0294) | 5.00 g (0.0294) | 5.00 g (0.0029) | 5.00 g (0.0029) |
|  |  | (C) | Water | 55 g | 55 g | 55 g | 55 g | 55 g |
|  | (A)/(B) molar ratio |  |  | 0.78 | 0.17 | 0.26 | 7.90 | 12.66 |
|  | [(A) + (B)]/(C) weight ratio |  |  | 0.109 | 0.055 | 0.073 | 0.093 | 0.147 |
|  | pH in second step (25° C.) |  |  | 4.5 | 4.5 | 4.5 | 4.5 | 4.5 |
| Organic peracid concentration (ppm) | Just after second step |  |  | 33500 | 36400 | 30100 | 4500 | 5300 |
|  | 30 minutes after second step |  |  | 30800 | 24100 | 28300 | 4300 | 5300 |
|  | 60 minutes after second step |  |  | 29600 | 22500 | 25100 | 4100 | 5000 |
| Degree of remaining organic peracid (%) |  |  |  | 88.4 | 85.2 | 83.4 | 91.1 | 94.3 |
| Degree of remaining hydrogen peroxide (%) |  |  |  | 6.9 | 30.9 | 21.1 | 25.9 | 17.4 |

TABLE 15

|  |  |  |  | Comparative Example |  |  |  |  |
|---|---|---|---|---|---|---|---|---|
|  |  |  |  | 5-1 | 5-2 | 5-3 | 5-4 | 5-5 |
| Manufacturing condition | Charging amount | (A) | Ethylene glycol diacetate | 0.2 g (0.0014) |  |  |  | 3 g (0.0205) |
|  |  |  | Triacetin |  | 0.2 g (0.0009) |  |  |  |
|  |  |  | Pentaacetyl-β-D-glucose |  |  | 0.2 g (0.0005) |  |  |
|  |  |  | Glycerin fatty acid ester |  |  |  | 0.2 g (0.0009) |  |
|  |  | (B) | Aqueous hydrogen peroxide (35 wt %) | 2.86 g (0.0294) | 2.86 g (0.0294) | 2.86 g (0.0294) | 2.86 g (0.0294) | 2.86 g (0.0294) |
|  |  |  | Sodium percarbonate |  |  |  |  |  |
|  |  |  | Sodium perborate |  |  |  |  |  |
|  |  | (C) | Water | 48 g | 48 g | 48 g | 55 g | 48 g |
|  | (A)/(B) molar ratio |  |  | 0.05 | 0.03 | 0.02 | 0.03 | 0.70 |
|  | [(A) + (B)]/(C) ratio by weight |  |  | 0.025 | 0.025 | 0.025 | 0.022 | 0.083 |
|  | pH in second step (25° C.) |  |  | 4.2 | 4.2 | 4.2 | 4.2 | 9.7 |

TABLE 15-continued

|  |  | 5-1 | 5-2 | 5-3 | 5-4 | 5-5 |
|---|---|---|---|---|---|---|
| Organic peracid concentration (ppm) | Just after second step | <1000 | 1800 | 2200 | <1000 | 22100 |
|  | 30 minutes after second step | <1000 | 1200 | 1500 | <1000 | 15300 |
|  | 60 minutes after second step | <1000 | <1000 | <1000 | <1000 | 8600 |
| Degree of remaining organic peracid (%) | | — | — | — | — | 38.9 |
| Degree of remaining hydrogen peroxide (%) | | 87.3 | 92.4 | 82.5 | 94.2 | 14.3 |

|  |  |  | Comparative Example |  |  |  |  |
|---|---|---|---|---|---|---|---|
|  |  |  | 5-6 | 5-7 | 5-8 | 5-9 | 5-10 |
| Manufacturing condition | Charging amount | (A) Ethylene glycol diacetate |  |  |  |  |  |
|  |  | Triacetin | 3 g (0.0138) |  |  | 5 g (0.0229) |  |
|  |  | Pentaacetyl-β-D-glucose |  | 3 g (0.0077) |  |  | 5 g (0.0128) |
|  |  | Glycerin fatty acid ester |  |  | 5 g (0.0229) |  |  |
|  |  | (B) Aqueous hydrogen peroxide (35 wt %) | 2.86 g (0.0294) | 2.86 g (0.0294) | 0.29 g (0.0030) | 2.86 g (0.0294) | 2.86 g (0.0294) |
|  |  | Sodium percarbonate |  |  |  |  |  |
|  |  | Sodium perborate |  |  |  |  |  |
|  |  | (C) Water | 48 g | 55 g | 55 g | 55 g | 55 g |
|  | (A)/(B) molar ratio |  | 0.47 | 0.26 | 7.63 | 0.78 | 0.44 |
|  | [(A) + (B)]/(C) ratio by weight |  | 0.083 | 0.073 | 0.093 | 0.109 | 0.109 |
|  | pH in second step (25° C.) |  | 9.7 | 9.7 | 9.7 | 8.3 | 8.3 |
| Organic peracid concentration (ppm) | Just after second step |  | 26100 | 29900 | 4500 | 33700 | 29900 |
|  | 30 minutes after second step |  | 17600 | 18600 | 2200 | 25500 | 24800 |
|  | 60 minutes after second step |  | 12900 | 13500 | <1000 | 15600 | 13800 |
| Degree of remaining organic peracid (%) |  |  | 49.4 | 45.2 | — | 46.3 | 46.2 |
| Degree of remaining hydrogen peroxide (%) |  |  | 13.2 | 10.3 | 7.9 | 5.3 | 5.1 |

TABLE 16

|  |  |  | Comparative Example |  |  |  |  |
|---|---|---|---|---|---|---|---|
|  |  |  | 5-11 | 5-12 | 5-13 | 5-14 | 5-15 |
| Manufacturing condition | Charging amount | (A) Ethylene glycol diacetate | 2 g (0.0014) |  |  |  | 3 g (0.0205) |
|  |  | Triacetin |  | 2 g (0.0009) |  |  |  |
|  |  | Pentaacetyl-β-D-glucose |  |  | 2 g (0.0005) |  |  |
|  |  | Glycerin fatty acid ester |  |  |  | 2 g (0.0009) |  |
|  |  | (B) Aqueous hydrogen peroxide (35 wt %) |  |  |  |  |  |
|  |  | Sodium percarbonate | 4.55 g (0.0294) | 4.55 g (0.0294) |  |  | 4.55 g (0.0294) |
|  |  | Sodium perborate |  |  | 5.00 g (0.0294) | 5.00 g (0.0294) |  |
|  |  | (C) Water | 55 g | 55 g | 55 g | 55 g | 55 g |
|  | (A)/(B) molar ratio |  | 0.05 | 0.03 | 0.02 | 0.03 | 0.70 |
|  | [(A) + (B)]/(C) ratio by weight |  | 0.022 | 0.022 | 0.022 | 0.022 | 0.073 |
|  | pH in second step (25° C.) |  | 4.5 | 4.5 | 4.5 | 4.5 | 9.2 |
| Organic peracid concentration (ppm) | Just after second step |  | <1000 | 1500 | 1800 | <1000 | 22000 |
|  | 30 minutes after second step |  | <1000 | 1000 | 1200 | <1000 | 16300 |
|  | 60 minutes after second step |  | <1000 | <1000 | <1000 | <1000 | 8500 |
| Degree of remaining organic peracid (%) |  |  | — | — | — | — | 38.6 |
| Degree of remaining hydrogen peroxide (%) |  |  | 87.3 | 88.6 | 86.3 | 91.8 | 15.0 |

|  |  |  | Comparative Example |  |  |  |  |
|---|---|---|---|---|---|---|---|
|  |  |  | 5-16 | 5-17 | 5-18 | 5-19 | 5-20 |
| Manufacturing condition | Charging amount | (A) Ethylene glycol diacetate |  |  |  |  |  |
|  |  | Triacetin | 3 g (0.0138) |  |  | 5 g (0.0229) |  |
|  |  | Pentaacetyl-β-D-glucose |  | 3 g (0.0077) |  |  | 5 g (0.0128) |
|  |  | Glycerin fatty acid ester |  |  | 5 g (0.0229) |  |  |
|  |  | (B) Aqueous hydrogen peroxide (35 wt %) |  |  |  |  |  |
|  |  | Sodium percarbonate | 4.55 g (0.0294) |  |  | 4.55 g (0.0294) |  |

TABLE 16-continued

|  |  |  |  |  |  |  |
|---|---|---|---|---|---|---|
|  | Sodium perborate |  | 5.00 g (0.0294) | 0.5 g (0.0029) |  | 5.00 g (0.0294) |
|  | (C) Water | 55 g | 55 g | 55 g | 55 g | 55 g |
|  | (A)/(B) molar ratio | 0.47 | 0.26 | 7.90 | 0.78 | 0.44 |
|  | [(A) + (B)]/(C) ratio by weight | 0.073 | 0.073 | 0.093 | 0.109 | 0.109 |
|  | pH in second step (25° C.) | 9.2 | 9.0 | 9.0 | 9.2 | 9.0 |
| Organic peracid concentration (ppm) | Just after second step | 27300 | 30100 | 4500 | 33500 | 35000 |
|  | 30 minutes after second step | 16300 | 20500 | 2000 | 24000 | 26400 |
|  | 60 minutes after second step | 11800 | 13700 | <1000 | 14900 | 16300 |
| Degree of remaining organic peracid (%) |  | 43.2 | 45.5 | — | 44.5 | 46.6 |
| Degree of remaining hydrogen peroxide (%) |  | 12.9 | 11.6 | 8.6 | 6.9 | 7.1 |

TABLE 17

|  |  |  |  | Comparative Example | | | | |
|---|---|---|---|---|---|---|---|---|
|  |  |  |  | 5-21 | 5-22 | 5-23 | 5-24 | 5-25 |
| Manufacturing condition | Charging amount | (A) | Ethylene glycol diacetate | 2 g (0.0137) | 5 g (0.0342) |  |  |  |
|  |  |  | Triacetin |  |  | 2 g (0.0092) |  |  |
|  |  |  | Pentaacetyl-β-D-glucose |  |  |  | 2 g (0.0051) |  |
|  |  |  | Glycerin fatty acid ester |  |  |  |  | 8 g (0.0367) |
|  |  | (B) | Aqueous hydrogen peroxide (35 wt %) | 2.86 g (0.0294) | 2.86 g (0.0294) | 2.86 g (0.0294) | 2.86 g (0.0294) | 0.29 g (0.0030) |
|  |  |  | Sodium percarbonate |  |  |  |  |  |
|  |  |  | Sodium perborate |  |  |  |  |  |
|  |  | (C) | Water | 48 g | 55 g | 48 g | 48 g | 60 g |
|  | (A)/(B) molar ratio |  |  | 0.47 | 1.16 | 0.31 | 0.17 | 12.23 |
|  | [(A) + (B)]/(C) ratio by weight |  |  | 0.063 | 0.109 | 0.063 | 0.063 | 0.135 |
|  | pH in second step (25° C.) |  |  | 9.5 | 9.5 | 9.5 | 8.6 | 8.6 |
| Organic peracid concentration (ppm) | Just after second step |  |  | 18300 | 23600 | 22300 | 26900 | 5500 |
|  | 30 minutes after second step |  |  | 10600 | 17700 | 17500 | 19900 | 3100 |
|  | 60 minutes after second step |  |  | 6800 | 10100 | 10300 | 13100 | 1900 |
| Degree of remaining organic peracid (%) |  |  |  | 37.2 | 42.8 | 46.2 | 48.7 | 34.5 |
| Degree of remaining hydrogen peroxide (%) |  |  |  | 43.2 | 21.6 | 39.5 | 28.4 | 6.7 |

|  |  |  |  | Comparative Example | | | | |
|---|---|---|---|---|---|---|---|---|
|  |  |  |  | 5-26 | 5-27 | 5-28 | 5-29 | 5-30 |
| Manufacturing condition | Charging amount | (A) | Ethylene glycol diacetate | 2 g (0.0137) | 5 g (0.0342) |  |  |  |
|  |  |  | Triacetin |  |  | 2 g (0.0092) |  |  |
|  |  |  | Pentaacetyl-β-D-glucose |  |  |  | 2 g (0.0051) |  |
|  |  |  | Glycerin fatty acid ester |  |  |  |  | 8 g (0.0367) |
|  |  | (B) | Aqueous hydrogen peroxide (35 wt %) |  |  |  |  |  |
|  |  |  | Sodium percarbonate | 4.55 g (0.0294) | 4.55 g (0.0294) | 4.55 g (0.0294) |  |  |
|  |  |  | Sodium perborate |  |  |  | 5.00 g (0.0294) | 0.5 g (0.0029) |
|  |  | (C) | Water | 55 g | 55 g | 55 g | 55 g | 55 g |
|  | (A)/(B) molar ratio |  |  | 0.47 | 1.16 | 0.31 | 0.17 | 12.66 |
|  | [(A) + (B)]/(C) ratio by weight |  |  | 0.055 | 0.109 | 0.055 | 0.055 | 0.147 |
|  | pH in second step (25° C.) |  |  | 9.2 | 9.2 | 9.2 | 9.0 | 9.0 |
| Organic peracid concentration (ppm) | Just after second step |  |  | 18500 | 23000 | 22100 | 26400 | 5300 |
|  | 30 minutes after second step |  |  | 11000 | 17500 | 18400 | 20900 | 3600 |
|  | 60 minutes after second step |  |  | 6700 | 10600 | 11000 | 12700 | 2000 |
| Degree of remaining organic peracid (%) |  |  |  | 36.2 | 46.1 | 49.8 | 48.1 | 37.7 |
| Degree of remaining hydrogen peroxide (%) |  |  |  | 38.7 | 21.7 | 42.1 | 27.6 | 7.7 |

TABLE 18

| | | | | Comparative Example | | | | |
|---|---|---|---|---|---|---|---|---|
| | | | | 5-31 | 5-32 | 5-33 | 5-34 | 5-35 |
| Manufacturing condition | Charging amount | (A) | Ethylene glycol diacetate | 2 g (0.0137) | 3 g (0.0205) | 5 g (0.0342) | | |
| | | | Triacetin | | | | 2 g (0.0092) | 3 g (0.0138) |
| | | | Pentaacetyl-β-D-glucose | | | | | |
| | | | Glycerin fatty acid ester | | | | | |
| | | (B) | Aqueous hydrogen peroxide (35 wt %) | 2.86 g (0.0294) | 2.86 g (0.0294) | 2.86 g (0.0294) | 2.86 g (0.0294) | 2.86 g (0.0294) |
| | | | Sodium percarbonate | | | | | |
| | | | Sodium perborate | | | | | |
| | | (C) | Water | 48 g | 48 g | 55 g | 48 g | 48 g |
| | (A)/(B) molar ratio | | | 0.47 | 0.70 | 1.16 | 0.31 | 0.47 |
| | [(A) + (B)]/(C) weight ratio | | | 0.063 | 0.083 | 0.109 | 0.063 | 0.083 |
| | pH in second step (25° C.) | | | 3~5 | 3~5 | 3~5 | 3~5 | 3~5 |
| Organic peracid concentration (ppm) | | | Just after preparation | <1000 | <1000 | <1000 | <1000 | <1000 |
| | | | 30 minutes after preparation | — | — | — | — | — |
| | | | 60 minutes after preparation | — | — | — | — | — |
| Degree of remaining organic peracid (%) | | | | — | — | — | — | — |
| Degree of remaining hydrogen peroxide (%) | | | | — | — | — | — | — |

| | | | | Comparative Example | | | | |
|---|---|---|---|---|---|---|---|---|
| | | | | 5-36 | 5-37 | 5-38 | 5-39 | 5-40 |
| Manufacturing condition | Charging amount | (A) | Ethylene glycol diacetate | | | | | |
| | | | Triacetin | 5 g (0.0229) | | | | |
| | | | Pentaacetyl-β-D-glucose | | 2 g (0.0051) | 3 g (0.0077) | | |
| | | | Glycerin fatty acid ester | | | | 5 g (0.0229) | 8 g (0.0367) |
| | | (B) | Aqueous hydrogen peroxide (35 wt %) | 2.86 g (0.0294) | 2.86 g (0.0294) | 2.86 g (0.0294) | 0.29 g (0.0030) | 0.29 g (0.0030) |
| | | | Sodium percarbonate | | | | | |
| | | | Sodium perborate | | | | | |
| | | (C) | Water | 55 g | 48 g | 55 g | 55 g | 60 g |
| | (A)/(B) molar ratio | | | 0.78 | 0.17 | 0.26 | 7.63 | 12.23 |
| | [(A) + (B)]/(C) weight ratio | | | 0.109 | 0.063 | 0.073 | 0.093 | 0.135 |
| | pH in second step (25° C.) | | | 3~5 | 3~5 | 3~5 | 3~5 | 3~5 |
| Organic peracid concentration (ppm) | | | Just after preparation | <1000 | <1000 | <1000 | <1000 | <1000 |
| | | | 30 minutes after preparation | — | — | — | — | — |
| | | | 60 minutes after preparation | — | — | — | — | — |
| Degree of remaining organic peracid (%) | | | | — | — | — | — | — |
| Degree of remaining hydrogen peroxide (%) | | | | — | — | — | — | — |

EXAMPLE 5a AND COMPARATIVE EXAMPLE 5a

Aqueous solutions for sterilization containing the organic peracids produced in Example 5 and Comparative Example 5, at concentrations shown in Tables 19 to 22, and having pH values shown in Table 19 to 22, were prepared and measured for their sterilizing effect by the following method. The results are shown in Tables 19 to 22.

(1) Sterilizing Effect of Microbial Spores

Spore-forming microorganisms *Bacillus subtilis* var. *niger* and *Bacillus circulans* IFO3967 were pre-cultured respectively in SCD agar mediums (manufactured by Nihon Pharmaceutical Co., Ltd.) at 30° C. for about 4 weeks, and a suitable amount of colonies formed on the agar medium was scratched away, suspended in 1 mL distilled water, and examined under a microscope to confirm the formation of microbial spores (referred to hereinafter as "spores"). This suspension was washed twice by centrifuge and then adjusted with a suitable amount of distilled water to a microbial density of about $10^8$ to $10^9$ cells/mL (spore suspension 1). 0.1 ml of the spore suspension 1 was put into 2 mL of each of the aqueous solutions for sterilization in Tables 19 to 22, to allow the aqueous solution to act thereon at 25° C. for 120 seconds. Immediately thereafter, 0.1 mL of the aqueous solution for sterilization containing the spore suspension 1 was added to an SCDLP medium (manufactured by Nihon Pharmaceutical Co., Ltd.) containing 1.0% sodium thiosulfate to inactivate the aqueous solution for sterilization (spore suspension 2). 0.2 mL of the spore suspension 2 was spread on a standard agar medium of 9 cm in diameter and cultured at 35° C. for 36 hours, and the number of colonies formed on the medium was counted to confirm the number of remaining bacteria.

(2) Sterilizing Effect of Fungal Spores

*Aspergillus niger* IFO6341 was pre-cultured in a potato dextrose agar medium (manufactured by Nihon Pharmaceutical Co., Ltd.) at 25° C. for about 4 weeks. Fungi formed on the agar medium were scratched away, suspended in 5 mL distilled water, and the fungal suspension was made uniform by a glass homogenizer. This suspension was washed twice by centrifuge and then adjusted with a suitable amount of distilled water to a microbial density of about $10^8$ to $10^9$ cells/mL (spore suspension 1). 0.1 ml of the spore suspension 1 was put into 2 mL of each of the aqueous solutions for sterilization in Tables 8 to 11, to allow the aqueous solution to act thereon at 25° C. for 120 seconds. Immediately thereafter, 0.1 mL of the aqueous solution for sterilization containing the spore suspension 1 was added to an SCDLP medium (manufactured by Nihon Pharmaceutical Co., Ltd.) containing 1.0% sodium thiosulfate to inactivate the aqueous solution for sterilization (spore suspension 2). 0.2 mL of the spore suspension 2 was spread on a potato dextrose agar medium of 9 cm in diameter and cultured at 25° C. for 3 to 4 days, and the number of colonies formed on the medium was counted to confirm the number of remaining fungi.

TABLE 19

|  |  |  | Example | | | | |
|---|---|---|---|---|---|---|---|
|  |  |  | 5a-1 | 5a-2 | 5a-3 | 5a-4 | 5a-5 |
| Aqueous solution for sterilization | Organic peracid | Production method | Example 5-1 | Example 5-2 | Example 5-3 | Example 5-4 | Example 5-5 |
|  |  | Concentration (ppm) | 4000 | 4000 | 4000 | 4000 | 4000 |
|  |  | pH (25° C.) | 4.0 | 4.0 | 4.0 | 4.0 | 4.0 |
| Number of remaining microorganisms (CFU/mL) | | *Bacillus subtilis* | <50 | <50 | <50 | <50 | <50 |
| | | *Bacillus circulans* | <50 | <50 | <50 | <50 | <50 |
| | | *Aspergillus niger* | <50 | <50 | <50 | <50 | <50 |

|  |  |  | Example | | | | |
|---|---|---|---|---|---|---|---|
|  |  |  | 5a-6 | 5a-7 | 5a-8 | 5a-9 | 5a-10 |
| Aqueous solution for sterilization | Organic peracid | Production method | Example 5-6 | Example 5-7 | Example 5-8 | Example 5-9 | Example 5-10 |
|  |  | Concentration (ppm) | 4000 | 4000 | 4000 | 4000 | 4000 |
|  |  | pH (25° C.) | 4.0 | 4.0 | 4.0 | 4.0 | 4.0 |
| Number of remaining microorganisms (CFU/mL) | | *Bacillus subtilis* | <50 | <50 | <50 | 50 | <50 |
| | | *Bacillus circulans* | <50 | <50 | <50 | 200 | 150 |
| | | *Aspergillus niger* | <50 | <50 | <50 | 250 | 100 |

TABLE 20

|  |  |  | Example | | | | |
|---|---|---|---|---|---|---|---|
|  |  |  | 5a-11 | 5a-12 | 5a-13 | 5a-14 | 5a-15 |
| Aqueous solution for sterilization | Organic peracid | Production method | Example 5-21 | Example 5-22 | Example 5-23 | Example 5-24 | Example 5-25 |
|  |  | Concentration(ppm) | 4000 | 4000 | 4000 | 4000 | 4000 |
|  |  | pH (25° C.) | 4.2 | 4.2 | 4.2 | 4.2 | 4.2 |
| Number of remaining microorganisms (CFU/mL) | | *Bacillus subtilis* | <50 | <50 | <50 | <50 | <50 |
| | | *Bacillus circulans* | <50 | <50 | <50 | <50 | <50 |
| | | *Aspergillus niger* | <50 | <50 | <50 | <50 | <50 |

|  |  |  | Example | | | | |
|---|---|---|---|---|---|---|---|
|  |  |  | 5a-16 | 5a-17 | 5a-18 | 5a-19 | 5a-20 |
| Aqueous solution for sterilization | Organic peracid | Production method | Example 5-26 | Example 5-27 | Example 5-28 | Example 5-29 | Example 5-30 |
|  |  | Concentration(ppm) | 4000 | 4000 | 4000 | 4000 | 4000 |
|  |  | pH (25° C.) | 4.2 | 4.2 | 4.2 | 4.2 | 4.2 |
| Number of remaining microorganisms (CFU/mL) | | *Bacillus subtilis* | <50 | <50 | <50 | 100 | 150 |
| | | *Bacillus circulans* | <50 | <50 | <50 | 250 | 200 |
| | | *Aspergillus niger* | <50 | <50 | <50 | 150 | 150 |

TABLE 21

|  |  |  | Comparative example | | | | |
|---|---|---|---|---|---|---|---|
|  |  |  | 5a-1 | 5a-2 | 5a-3 | 5a-4 | 5a-5 |
| Aqueous solution for sterilization | Organic peracid | Prouction method | Comparative example 5-5 | Comparative example 5-6 | Comparative example 5-7 | Comparative example 5-8 | Comparative example 5-9 |
|  |  | Concentration (ppm) | 4000 | 4000 | 4000 | 4000 | 4000 |
|  |  | pH (25° C.) | 9.5 | 9.5 | 8.6 | 8.6 | 9.5 |
| Number of remaining microorganisms (CFU/mL) | | *Bacillus subtilis* | $6.7 \times 10^7$ | $6.2 \times 10^7$ | $7.4 \times 10^6$ | $9.8 \times 10^6$ | $6.1 \times 10^7$ |
| | | *Bacillus circulans* | $5.3 \times 10^7$ | $4.8 \times 10^7$ | $1.1 \times 10^7$ | $1.0 \times 10^7$ | $4.3 \times 10^7$ |
| | | *Aspergillus niger* | $8.7 \times 10^7$ | $1.6 \times 10^7$ | $6.9 \times 10^5$ | $7.7 \times 10^5$ | $7.1 \times 10^7$ |

TABLE 21-continued

|  |  |  | Comparative example | | | | |
|---|---|---|---|---|---|---|---|
|  |  |  | 5a-6 | 5a-7 | 5a-8 | 5a-9 | 5a-10 |
| Aqueous solution for sterilization | Organic peracid | Prouction method | Comparative example 5-15 | Comparative example 5-16 | Comparative example 5-17 | Comparative example 5-18 | Comparative example 5-19 |
|  |  | Concentration (ppm) | 4000 | 4000 | 4000 | 4000 | 4000 |
|  | pH (25° C.) |  | 9.2 | 9.2 | 9.0 | 9.0 | 9.2 |
| Number of remaining microorganisms (CFU/mL) | Bacillus subtilis |  | $7.9 \times 10^7$ | $6.8 \times 10^7$ | $4.3 \times 10^6$ | $9.1 \times 10^6$ | $7.2 \times 10^7$ |
|  | Bacillus circulans |  | $6.1 \times 10^7$ | $5.7 \times 10^7$ | $9.7 \times 10^6$ | $1.6 \times 10^7$ | $5.9 \times 10^7$ |
|  | Aspergillus niger |  | $3.8 \times 10^7$ | $4.3 \times 10^7$ | $3.8 \times 10^7$ | $1.7 \times 10^7$ | $4.1 \times 10^7$ |

TABLE 22

|  |  |  | Comparative example | | | | |
|---|---|---|---|---|---|---|---|
|  |  |  | 5a-11 | 5a-12 | 5a-13 | 5a-14 | 5a-15 |
| Aqueous solution for sterilization | Organic peracid | Production method | Comparative example 5-21 | Comparative example 5-22 | Comparative example 5-23 | Comparative example 5-24 | Comparative example 5-25 |
|  |  | Concentration (ppm) | 4000 | 4000 | 4000 | 4000 | 4000 |
|  | pH (25° C.) |  | 9.5 | 9.5 | 9.5 | 8.6 | 8.6 |
| Number of remaining microorganisms (CFU/mL) | Bacillus subtilis |  | $6.8 \times 10^7$ | $5.9 \times 10^7$ | $6.1 \times 10^7$ | $8.6 \times 10^8$ | $1.0 \times 10^7$ |
|  | Bacillus circulans |  | $5.1 \times 10^7$ | $5.0 \times 10^7$ | $4.2 \times 10^7$ | $9.9 \times 10^6$ | $1.3 \times 10^7$ |
|  | Aspergillus niger |  | $1.6 \times 10^7$ | $9.1 \times 10^7$ | $7.2 \times 10^7$ | $8.5 \times 10^5$ | $7.8 \times 10^5$ |
|  |  |  | Comparative example | | | | |
|  |  |  | 5a-16 | 5a-17 | 5a-18 | 5a-19 | 5a-20 |
| Aqueous solution for sterilization | Organic peracid | Production method | Comparative example 5-26 | Comparative example 5-27 | Comparative example 5-28 | Comparative example 5-29 | Comparative example 5-30 |
|  |  | Concentration (ppm) | 4000 | 4000 | 4000 | 4000 | 4000 |
|  | pH (25° C.) |  | 9.2 | 9.2 | 9.2 | 9.0 | 9.0 |
| Number of remaining microorganisms (CFU/mL) | Bacillus subtilis |  | $7.1 \times 10^7$ | $7.2 \times 10^7$ | $6.9 \times 10^7$ | $4.3 \times 10^6$ | $1.5 \times 10^7$ |
|  | Bacillus circulans |  | $6.3 \times 10^7$ | $5.3 \times 10^7$ | $5.4 \times 10^7$ | $1.6 \times 10^7$ | $1.1 \times 10^7$ |
|  | Aspergillus niger |  | $2.5 \times 10^7$ | $1.9 \times 10^7$ | $5.6 \times 10^7$ | $2.2 \times 10^7$ | $2.1 \times 10^7$ |

EXAMPLE 6

Deionized water was added to the components (A) and (B), organic phosphonic acid (trade name: Dequest 2010, manufactured by Solutia Japan Ltd.) and an alkaline pH adjusting agent in the amounts shown in Table 23, to adjust the total weight of the mixture to 100 g (first step). This mixture was mixed for about 10 minutes with stirring in a 200 mL beaker. The pH in this step was 8 to 12. Thereafter, the mixture was rapidly adjusted to the objective pH by using an acidic pH adjusting agent in a weight shown in Table 21, followed by adding deionized water to adjust the total amount to 110 g (second step). At this point in time (just after preparation), the mixture was measured for organic peracid concentration and hydrogen peroxide concentration, and a change in the organic peracid concentration with time (just after preparation, 30 minutes, 60 minutes and 120 minutes after preparation) was measured. After 120 minutes, the aqueous solution for sterilization was adjusted to an organic peracid concentration of 3000 ppm, and its sterilizing effect was confirmed. The method of measuring the hydrogen peroxide concentration and the organic peracid concentration was conducted according to the method of measuring the organic peracid concentration in Example 5. The sterilization test method was in accordance with measurement of sterilizing effect of bacterial spores in Example 5a, but in this example, the temperature and time for contacting the aqueous solution for sterilization with bacteria were 60° C. and 20 seconds respectively, and as the objective bacteria, Bacillus cereus IFO13494 and Bacillus circulans IFO3967 were used.

TABLE 23

|  |  |  | Example | | | | |
|---|---|---|---|---|---|---|---|
|  |  |  | 6-1 | 6-2 | 6-3 | 6-4 | 6-5 |
| Compounding ingredients | (A) | Ethylene glycol diacetate | 5 g (0.0342) | 5 g (0.0342) |  |  |  |
|  |  | Triacetin |  |  | 5 g (0.0229) | 5 g (0.0229) | 5 g (0.0229) |
|  |  | Pentaacetyl-β-D-glucose |  |  |  |  |  |

TABLE 23-continued

|  |  |  |  |  |  |  |  |
|---|---|---|---|---|---|---|---|
|  | (B) | Aqueous hydrogen peroxide (35 wt %) | 4.3 g (0.0443) | 4.3 g (0.0443) | 4.3 g (0.0443) | 4.3 g (0.0443) | 4.3 g (0.0443) |
|  | Chelating agent (net content) | Organic phosphonic acid | 0.1 g | 0.1 g | 0.1 g | 0.1 g | 0.1 g |
|  | Alkaline pH adjusting agent (net content) | Sodium hydroxide | 2 g |  | 2 g |  |  |
|  |  | Sodium carbonate |  |  |  | 6 g |  |
|  |  | Trisodium phosphoate |  | 4 g |  |  | 4 g |
|  | Acidic pH adjusting agent | Sulfuric acid (purity 98%) | 2.1 g | 2.1 g |  |  |  |
|  |  | Phosphoric acid (purity 85%) | 0.5 g | 0.5 g | 5.0 g | 5.0 g | 5.0 g |
| (A)/(B) molar ratio |  |  | 0.77 | 0.77 | 0.52 | 0.52 | 0.52 |
| Organic peracid concentration (ppm) |  | Just after preparation | 25,000 | 24,000 | 27,000 | 22,000 | 26,000 |
|  |  | 30 minutes later | 25,000 | 23,500 | 26,500 | 20,000 | 25,500 |
|  |  | 60 minutes later | 24,500 | 23,000 | 26,500 | 19,000 | 25,000 |
|  |  | 120 minutes later | 24,000 | 22,000 | 25,000 | 18,000 | 24,000 |
| Hydrogen peroxide concentration (ppm) just after preparation |  |  | 1,500 | 1,650 | 1,050 | 1,900 | 1,350 |
| pH of aqueous solution for sterilization (25° C.) |  |  | 3.5 | 2.8 | 3.7 | 1.5 | 3.0 |
| Number of remaining microorganisms (CFU/mL) |  | Bacillus cereus IFO13494 | <50 | <50 | <50 | <50 | <50 |
|  |  | Bacillus subtilis var. niger | <50 | <50 | <50 | <50 | <50 |

|  |  |  | Example |  |  |  |  |
|---|---|---|---|---|---|---|---|
|  |  |  | 6-6 | 6-7 | 6-8 | 6-9 | 6-10 |
| Compounding ingredients | (A) | Ethylene glycol diacetate |  |  |  |  |  |
|  |  | Triacetin | 5 g (0.0229) | 5 g (0.0229) | 5 g (0.0229) |  |  |
|  |  | Pentaacetyl-β-D-glucose |  |  |  | 5 g (0.0128) | 5 g (0.0128) |
|  | (B) | Aqueous hydrogen peroxide (35 wt %) | 4.3 g (0.0443) | 4.3 g (0.0443) | 4.3 g (0.0443) | 4.3 g (0.0443) | 4.3 g (0.0443) |
|  | Chelating agent (net content) | Organic phosphonic acid | 0.1 g | 0.1 g | 0.1 g | 0.1 g | 0.1 g |
|  | Alkaline pH adjusting agent (net content) | Sodium hydroxide | 2 g |  |  | 2 g |  |
|  |  | Sodium carbonate |  | 6 g |  |  |  |
|  |  | Trisodium phosphoate |  |  | 4 g |  | 4 g |
|  | Acidic pH adjusting agent | Sulfuric acid (purity 98%) | 2.1 g | 2.1 g | 2.1 g | 2.1 g | 2.1 g |
|  |  | Phosphoric acid (purity 85%) | 0.5 g | 0.5 g | 0.5 g | 0.5 g | 0.5 g |
| (A)/(B) molar ratio |  |  | 0.52 | 0.52 | 0.52 | 0.29 | 0.29 |
| Organic peracid concentration (ppm) |  | Just after preparation | 27,000 | 22,000 | 26,000 | 30,000 | 29,500 |
|  |  | 30 minutes later | 26,000 | 20,000 | 25,500 | 28,000 | 28,000 |
|  |  | 60 minutes later | 25,500 | 19,000 | 24,000 | 27,000 | 27,000 |
|  |  | 120 minutes later | 25,000 | 18,000 | 23,500 | 25,500 | 25,500 |
| Hydrogen peroxide concentration (ppm) just after preparation |  |  | 1,050 | 1,850 | 1,300 | 900 | 950 |
| pH of aqueous solution for sterilization (25° C.) |  |  | 3.5 | 1.2 | 2.8 | 3.5 | 2.8 |
| Number of remaining microorganisms (CFU/mL) |  | Bacillus cereus IFO13494 | <50 | <50 | <50 | <50 | <50 |
|  |  | Bacillus subtilis var. niger | <50 | <50 | <50 | <50 | <50 |

EXAMPLE 7

Liquid compositions having the compositions shown in Table 24 were prepared and evaluated for the stability of organic peracid formation by the following method. The results are shown in Table 24.

<Organic Peracid Formation Stability Test Method>

Deionized water was added to X g liquid composition in Table 24, 0.1 g organic phosphonic acid and 2 g NaOH in a 100 mL beaker to adjust the total amount to 100 g. This mixture was mixed for about 5 minutes with stirring, and then the concentration of formed organic peracid (%) (concentration of formed organic peracid just after preparation) was measured according to the method of measuring the organic peracid concentration in Example 5. In Examples 7-1 to 7-3, X was 7.5 (g), and in Examples 7-4 to 7-9 and Comparative Examples 7-1 to 7-2, X was 10 (g).

A 200 ml glass bottle (colorless and transparent) was charged with 150 ml liquid composition in Table 24, then capped and stored at 50° C. After 4 weeks, an organic peracid was formed in the same manner as described above, and the concentration (%) of the formed organic peracid after storage was measured in the same manner. Organic peracid formation stability was determined according to the following equation:

Organic peracid formation stability(%)=[(concentration of formed organic peracid after storage)/(concentration of formed organic peracid just after preparation)]×100

TABLE 24

|  |  |  |  | Example |  |  |  |  |  |
|---|---|---|---|---|---|---|---|---|---|
|  |  |  |  | 7-1 | 7-2 | 7-3 | 7-4 | 7-5 | 7-6 |
| Composition for starting materials | Composition (wt %) | (A) | Triacetin | 66.7 |  |  | 50 |  |  |
|  |  |  | Diacetin |  | 66.7 |  |  | 50 |  |
|  |  |  | Ethylene glycol diacetate |  |  | 66.7 |  |  | 50 |
|  |  |  | Glycerin fatty acid ester[X-1] |  |  |  |  |  |  |

TABLE 24-continued

|  |  |  |  |  |  |  |  |
|---|---|---|---|---|---|---|---|
|  | (B) Hydrogen peracid | 20 | 20 | 20 | 15 | 15 | 15 |
|  | 1-Hydroxyethylidene-1,1-diphosphonic acid[X2] |  |  |  |  |  |  |
|  | NaOH[X3] |  |  |  |  |  |  |
|  | Propylene glycol |  |  |  | 25 | 25 | 25 |
|  | Water | 13.3 | 13.3 | 13.3 | 10 | 10 | 10 |
|  | Total | 100.0 | 100.0 | 100.0 | 100.0 | 100.0 | 100.0 |
|  | Compounded state (visual check) | ○ | ○ | ○ | ○ | ○ | ○ |
|  | pH (stock solution, 20° C.) | 3.0 | 3.3 | 4.5 | 3.1 | 3.5 | 4.7 |
| Concentration of formed organic peracid (ppm) | Just after preparation (before storage) | 31350 | 27360 | 28310 | 31350 | 27360 | 28310 |
|  | After storage | 28880 | 16340 | 22800 | 21280 | 13680 | 20900 |
| Organic peracid formation stability (%) |  | 92 | 60 | 81 | 68 | 50 | 74 |

|  |  |  | Example | | | Comparative example | |
|---|---|---|---|---|---|---|---|
|  |  |  | 7-7 | 7-8 | 7-9 | 7-1 | 7-2 |
| Composition for starting materials | Composition (wt %) | (A) Triacetin |  | 50 | 50 | 50 |  |
|  |  | Diacetin |  |  |  |  | 50 |
|  |  | Ethylene glycol diacetate |  |  |  |  |  |
|  |  | Glycerin fatty acid ester[X1] | 50 |  |  |  |  |
|  | (B) Hydrogen peracid |  | 15 | 15 | 15 | 15 | 15 |
|  | 1-Hydroxyethylidene-1,1-diphosphonic acid[X2] |  |  | 0.50 |  |  |  |
|  | NaOH[X3] |  |  | 0.17 |  |  |  |
|  | Propylene glycol |  | 25 | 24 | 15 | 5 |  |
|  | Water |  | 10 | 10.33 | 20 | 30 | 35 |
|  | Total |  | 100.0 | 100.0 | 100.0 | 100.0 | 100.0 |
|  | Compounded state (visual check) |  | ○ | ○ | ○ | ○ | ○ |
|  | pH (stock solution, 20° C.) |  | 3.8 | 3.1 | 2.8 | 2.9 | 3.4 |
| Concentration of formed organic peracid (ppm) | Just after preparation (before storage) |  | 7200 | 31350 | 29830 | 30400 | 29830 |
|  | After storage |  | 5600 | 16340 | 13680 | 6460 | 7220 |
| Organic peracid formation stability (%) |  |  | 78 | 52 | 46 | 21 | 24 |

[X1]Homotex PT(trade name, manufactured by Kao corporation), an ester of glycerin and C8 fatty acid
[X2]Dequest 2010 (trade name, manufactured by Solutia Japan Ltd.), 60 wt % active ingredient, 40 wt % water
[X3]48 wt % active ingredient, 52 wt % water

The invention claimed is:

1. A method of sterilizing a material to be sterilized, which comprises contacting, with a material to be sterilized, an aqueous solution containing an organic peracid obtained by reacting (A) an ester of a polyhydric alcohol and an organic acid having a hydrocarbon group which may have a hydroxyl group with (B1) hydrogen peroxide in an (A)/(B1) molar ratio of 1/5 to 10/1 in water adjusted to a pH of 8 to 12 with an alkaline pH adjusting agent, and then adjusting the reaction system to pH 1 to 5;
wherein the reaction of (A) with (B1) in water at pH 8 to 12 is carried out at 5 to 50° C. for 1 to 120 minutes, and
a molar ratio of the component (B1) to one ester group of the component (A) is 2 or less.

2. The sterilizing method according to claim 1, wherein the content of hydrogen peroxide is 0.5 wt % or less.

3. A process for producing an organic peracid, which comprises a step of reacting (A) an ester of a polyhydric alcohol and an organic acid having a hydrocarbon group which may have a hydroxyl group with (B1) hydrogen peroxide in an (A)/(B1) molar ratio of 1/5 to 10/1 in water adjusted to a pH of 8 to 12 with an alkaline pH adjusting agent, and then adjusting the reaction system to pH 1 to 5;
wherein the reaction of (A) with (B1) in water at pH 8 to 12 is carried out at 5 to 50° C. for 1 to 120 minutes, and
a molar ratio of the component (B1) to one ester group of the component (A) is 2 or less.

4. A process for producing a sterilizer composition, which comprises a step of reacting (A) an ester of a polyhydric alcohol and an organic acid having a hydrocarbon group which may have a hydroxyl group with (B1) hydrogen peroxide in an (A)/(B1) molar ratio of 1/5 to 10/1 in water adjusted to a pH of 8 to 12 with an alkaline pH adjusting agent, and then adjusting the reaction system to pH 1 to 5;
wherein the reaction of (A) with (B1) in water at pH 8 to 12 is carried out at 5 to 50° C. for 1 to 120 minutes, and
a molar ratio of the component (B1) to one ester group of the component (A) is 2 or less.

5. The process according to claim 4, wherein the content of hydrogen peroxide in the sterilizer composition is 0.5 wt % or less.

6. The process according to claim 4, wherein the polyhydric alcohol constituting (A) is a C2 to C12 polyhydric alcohol.

7. The process according to claim 4, wherein the organic acid constituting (A) is a C1 to C8 fatty acid.

8. The sterilizing method according to claim 1, wherein the pH of the reaction system before adjustment is 9 to 11.

9. The process according to claim 3, wherein the pH of the reaction system before adjustment is 9 to 11.

10. The process according to claim 4, wherein the pH of the reaction system before adjustment is 9 to 11.

11. The sterilizing method according to claim 1, wherein the reaction system is adjusted to pH 3.8 to 5.

12. The process according to claim 3, wherein the reaction system is adjusted to pH 3.8 to 5.

13. The process according to claim 4, wherein the reaction system is adjusted to pH 3.8 to 5.

* * * * *